United States Patent
Guo et al.

(10) Patent No.: US 11,478,352 B2
(45) Date of Patent: Oct. 25, 2022

(54) VENOUS VALVE REPLACEMENT DEVICE

(71) Applicant: Hangzhou Nuoyi Medtech Co., Ltd, Zhejiang (CN)

(72) Inventors: Wei Guo, Shanghai (CN); Yongsheng Wang, Shanghai (CN); Jianmin Li, Shanghai (CN); Jiaming Qiu, Shanghai (CN)

(73) Assignee: HANGZHOU NUOYI MEDTECH CO., LTD, Zhejiang (CN)

( * ) Notice: Subject to any disclaimer, the term of this patent is extended or adjusted under 35 U.S.C. 154(b) by 113 days.

(21) Appl. No.: 17/046,086

(22) PCT Filed: Apr. 9, 2019

(86) PCT No.: PCT/CN2019/081973
§ 371 (c)(1),
(2) Date: Oct. 8, 2020

(87) PCT Pub. No.: WO2019/196845
PCT Pub. Date: Oct. 17, 2019

(65) Prior Publication Data
US 2021/0059819 A1    Mar. 4, 2021

(30) Foreign Application Priority Data
Apr. 9, 2018    (CN) .......................... 201810311380.9

(51) Int. Cl.
*A61F 2/24*    (2006.01)
(52) U.S. Cl.
CPC .......... *A61F 2/2475* (2013.01); *A61F 2/2418* (2013.01); *A61F 2230/0054* (2013.01)

(58) Field of Classification Search
CPC .... A61F 2/2475; A61F 2/2412; A61F 2/2415; A61F 2/2418
See application file for complete search history.

(56) References Cited

U.S. PATENT DOCUMENTS

| | | | |
|---|---|---|---|
| 5,489,297 A | 2/1996 | Duran | |
| 2004/0243222 A1 | 12/2004 | Osborne et al. | |
| 2006/0161248 A1 | 7/2006 | Case et al. | |
| 2017/0189175 A1* | 7/2017 | Justino | ................ A61F 2/2418 |

FOREIGN PATENT DOCUMENTS

| | | |
|---|---|---|
| CN | 104039271 | 9/2014 |
| CN | 107106294 | 8/2017 |

OTHER PUBLICATIONS

Extended European Search Report of Application No. EP19785321 dated Dec. 22, 2021, 8 pages.
International Search Report and Written Opinion of PCT/CN2019/081973 dated Jul. 25, 2019, 12 pages (English and Chinese).

* cited by examiner

*Primary Examiner* — Suba Ganesan
(74) *Attorney, Agent, or Firm* — Rankin, Hill & Clark LLP

(57) ABSTRACT

A venous valve replacement device includes a stent with a blood flow channel and two leaflets connected to the stent, wherein one side of each leaflet is configured as a fixed edge connected with the stent, and the other side is configured as a movable edge, and wherein the movable edges of the two leaflets cooperates with each other to open or close the blood flow channel, and the movable edges of the two leaflets are provided with flaps that attach to each other in a closed configuration.

19 Claims, 18 Drawing Sheets

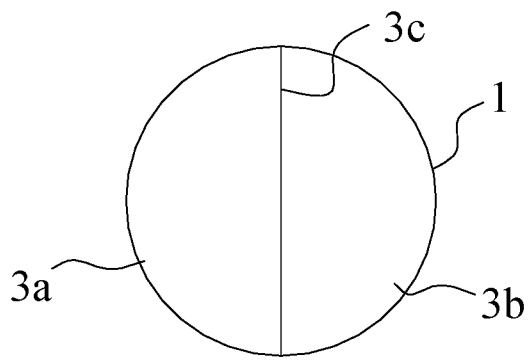
FIG. 9a
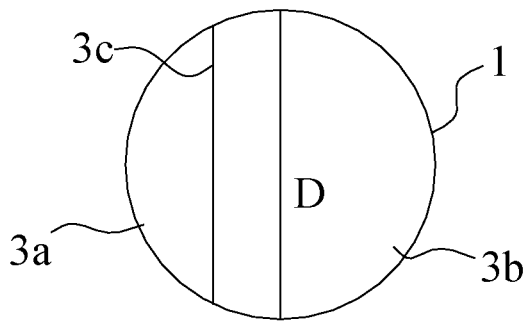
FIG. 9b
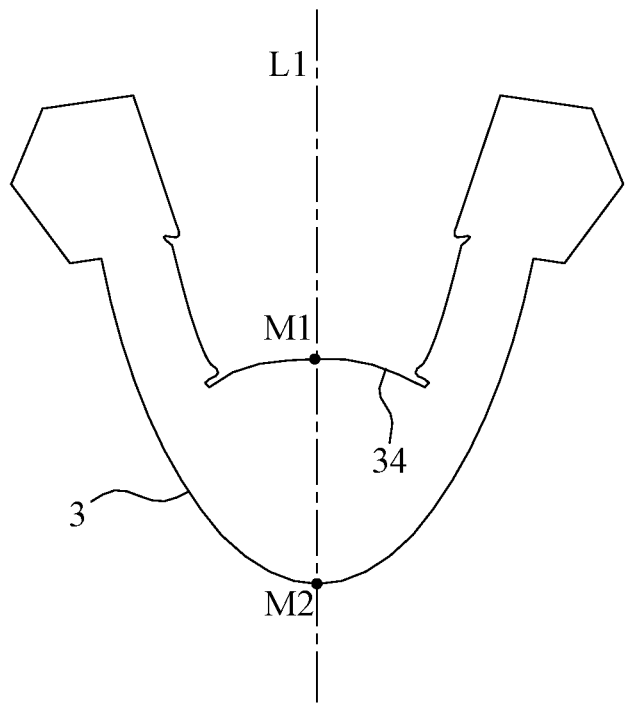
FIG. 10
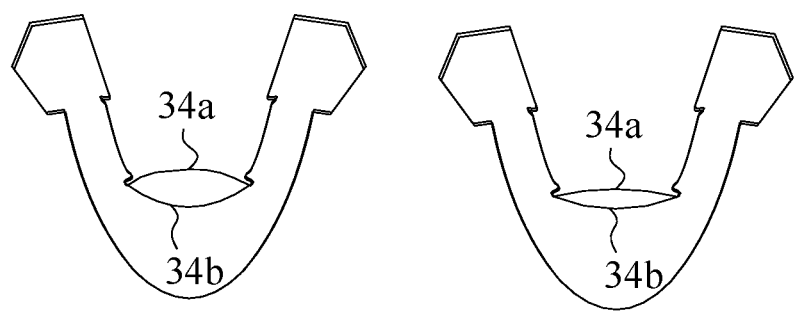
FIG. 11a
FIG. 11b

VENOUS VALVE REPLACEMENT DEVICE

TECHNICAL FIELD

This disclosure relates to the technical field of medical devices, and in particular to a venous valve replacement device, which can be implanted into the human body by intervention to improve reflux of venous blood.

BACKGROUND

In order to relieve and treat reflux of venous blood, a variety of artificial venous valves and the usage methods thereof are known in the art. Some of the products have complex structures and poor reliability, and some of the products include relatively simple meshed stents combined with leaflet. A single leaflet, two leaflets or three leaflets may be provided.

The rate of the venous blood flow is slow, and the leaflets are required to open or close flexibly. Three leaflets are difficult to meet this requirement. However, the single leaflet and the two leaflets are difficult to balance the opening area and the sealing performance of the channel.

Furthermore, when the leaflets are closed, a thrombus between the leaflet and the stent on the upstream of the normal blood flow would be formed easily, which is also an urgent problem to be solved.

SUMMARY

The present disclosure provides a venous valve replacement device, which, based on two leaflets that can open or close flexibly, improves the structure and solves the existing problems, and has good sealing performance.

A venous valve replacement device includes a stent with a blood flow channel and two leaflets connected to the stent, wherein one side of each leaflet is configured as a fixed edge connected with the stent, and the other side is configured as a movable edge, and wherein the movable edges of the two leaflets cooperates with each other to open or close the blood flow channel, and the movable edges of the two leaflets are provided with flaps that attach to each other in a closed configuration.

A plurality of alternative implementations is provided below. These alternative implementations are not intended as additional limitations to the above-mentioned overall technical solution, but merely as further additions or optimizations. Without technical or logical contradiction, these alternative implementations can be combined with the above-mentioned overall technical solution, respectively or in combination.

The stent in this disclosure can use the existing technology. The stent has a cylindrical structure to adapt to the shape of the intravenous cavity. The cylindrical structure does not need to be a complete cylinder, provided that at least one supporting ring supporting the intravenous cavity and a supporting structure corresponding to the shape of the fixed edge are provided by the cylindrical structure. The stent may adopt a radial compressible meshed structure, which can be compressed and released easily, and may be formed, for example, by weaving or cutting. The meshed structure may include regular or irregular grids.

The material of the leaflet itself may use the existing technology. For example, the material of the leaflet may use biomembranes such as porcine pericardium or bovine pericardium. The leaflet is fixed on the stent by means of stitching or the like. The improvement of this disclosure focuses on the use of two leaflets as well as the shape of the leaflets. The movable edges of the two leaflets form a one-way valve structure, which opens under the action of normal venous blood flow (hereinafter referred to as normal blood flow), while attach to each other to seal and close to prevent venous reflux when the blood pressure changes. The flaps play a guiding role during the closing process.

Because the flaps protrude from the movable edge, under the action of back-flow blood, two flaps that cooperate with each other will move closer to each other more easily, so that the leaflet where the flap is located will move closer to the other leaflet, thereby the movable edges of the leaflets will attach to each other and close.

Furthermore, after the leaflets are closed, the two flaps that cooperate with each other overlap with each other and have a large contact area. Compared with other portions of the movable edges that are attached to each other only at the edges, the two flaps have a better locking effect, and further ensure the sealing performance.

Optionally, the flap and the leaflet are formed in one piece.

One-piece material is easier to process, and the portion of the flap connected with the movable edge has a better strength. In order to avoid local stress concentration, the flap transitions to the movable edge through a smooth edge.

Optionally, the flap protrudes from the corresponding movable edge.

As a whole, the movable edge is shaped as a continuous curve, and the extending trend of the movable edge suddenly and locally changes at the flap. Because the flaps need to guide the leaflets to close and lock together, each flap generally protrudes from the movable edge where it is located.

Optionally, the area of the flap ranges from 0.1 to 10 square millimeters, more preferably, from 4 square millimeters to 6 square millimeters.

Optionally, the fixed edge is shaped as a parabola, wherein the apex is located at the upstream of the normal blood flow, and the fixed edge gradually extends towards the downstream of the normal blood flow from the apex on both sides.

The flap should have a certain area to play a guiding role, but if the area is too large, it will bring additional resistance to the opening of the movable edges and reduce the flexibility of the one-way valve to open.

Optionally, the flaps on the two leaflets have the matched position and the same shape.

If the flaps only need to guide the leaflets to close, the flaps on the two leaflets are not required to have the consistent position, and it is possible to make one flap offset from the other. However, if the flaps need to lock and close, they should be at least attachable to each other locally, or even be locally deformable to surround one the other.

Optionally, the middle portion of the movable edge protrudes toward the fixed edge or protrudes away from the fixed edge, and the apex of the protruding portion is the apex of the movable edge. Because the fixed edge is fixed to the inner wall of the stent, and in combination with the profiles of the two leaflets, the fixed edge is generally parabolic. It should be noted that "The middle portion of the movable edge protrudes towards or away from the fixed edge" is to define the general tendency. For example, the middle portion of the movable edge may be arc-shaped, and the direction of the apex of the arc may be regarded as the protruding direction. The technique of using an arc shape can appropriately increase the length of the two movable edges and increase the cross-sectional area of the channel when opening.

Optionally, the same leaflet is provided with two flaps, and the two flaps are respectively located on both sides of the apex of the movable edge.

At least one flap is provided on the movable edge of each leaflet. In order to improve the effect, the number of flaps can be appropriately increased. In the preferred implementation, two flaps are provided on the movable edge of each leaflet to improve the sealing performance after being closed. The flap should avoid being located at the middle portion of the movable edge. The middle portion of the movable edge refers to the middle portion in the extension direction of the movable edge. For example, in the case where the movable edge is shaped as a curve, the middle portion refers to the portion near the middle point of the curve.

Optionally, the two flaps are symmetrically distributed on both sides of the apex of the movable edge.

Two symmetrical flaps on the same leaflet make the movements of the two sides of the leaflet more consistent with each other. If one side is closed first, the other side may be severely deformed under the action of blood flow and the closing effect would be affected.

Optionally, the two leaflets are formed in one piece.

Two leaflets can be cut out at one time through a one piece material, and then can be enclosed into a cylinder and stitched on the stent.

Optionally, in the closed configuration, the movable edge extends in a two-dimensional plane.

Optionally, in the closed configuration, the projection of the movable edge along the axial direction of the stent is a straight line segment.

Optionally, the intersection line of the movable edges of the two leaflets in the closed configuration passes through the axis of the stent or is offset from the axis of the stent.

Optionally, in the flattened configuration of the leaflet, the middle portion of the fixed edge protrudes away from the movable edge, and the apex of the protruding portion at the middle portion of the fixed edge is the apex of the fixed edge, and the apex of the protruding portion at the middle portion of the movable edge is the apex of the movable edge.

Both the fixed edge and the movable edge are generally shaped as a parabola. The apexes of the fixed edge and the movable edge are approximately located at their respective midpoints. The portion of the movable edge near the apex protrudes towards or away from the fixed edge as described above.

Optionally, the line connecting the apex of the movable edge and the apex of the fixed edge is the centerline of the leaflet.

Each leaflet is preferred to be formed as a symmetrical structure, and the centerline of the leaflet is the axis of symmetry of the leaflet.

Two sets of threading holes are provided on the stent, which are located on both sides of the apex of the fixed edge of the same leaflet. For example, each set of threading holes may include 3 to 10 threading holes.

Optionally, the portions of the movable edge and the fixed edge on the same side of the centerline of the leaflet are gradually closer to each other and are connected by a patch, which is connected to the stent.

The patch functions to strengthen the tip of the leaflet, i.e., the intersection of the fixed edge and the movable edge. Also, the patch can be easily stitched on the stent. There is no strict restriction on the shape of the patch. In general, the shape of the patch corresponds to that of the corresponding grid where the patch is positioned, and can just cover the corresponding grid and be stitched on the supporting bar around the grid.

Optionally, the angle between the centerline of the leaflet and the axis of the stent in the closed configuration ranges from 30 to 60 degrees, preferably, from 30 to 45 degrees.

The angle between the centerline of the leaflet and the axis of the stent generally reflects the angle between the two leaflets in the closed configuration, and the angle affects the flexibility of the leaflets to open or close.

If the angle between the centerline of the leaflet and the axis of the stent is too large, for example, close to 90 degrees, the two leaflets are almost coplanar, which will require a stronger blood flow to open the movable edges, and it is not easy to form a large opening. Obviously, venous blood with a slow flow rate cannot meet this requirement.

If the angle is too small, the fixed edge and the movable edge of the leaflet will extend a long distance in the axial direction to meet. The movable edges have great deformation to open or close. However, too great deformation will result in poor sealing.

Optionally, the movable edge is provided with a notch adjacent to the patch to increase the relative degree of freedom.

The movable edge extends to the end (the end away from the apex of the movable edge), and is connected with the patch. Since the patch is fixed on the stent, it will affect the freedom of the movable edge, that is, it will restrain the movable edge. The notch can reduce the influence from the patch to the movement of the movable edge, and improve and increase the flexibility of the opening or closing of the movable edges.

Optionally, the profile of the notch is shaped as a smooth curve.

The profile is shaped as a smooth curve, which can avoid local stress concentration and reduce the risk of tearing during the stretching process.

Optionally, the movable edge includes a mouth section located near the apex of the movable edge, and guide sections respectively located on both sides of the mouth section, wherein the radial outward extending rate is V1, the radial outward extending rate of the guide section is V2, and V1 is greater than V2.

The radial outward extending rate is the variation of the radial position when extending for a unit distance along the axial direction of the stent.

The mouth section is relatively straight (the extension direction thereof is closer to the radial direction of the stent), which can improve the speed and the flexibility of opening or closing. The guide section is longer and steeper (the extension direction thereof is closer to axial direction of the stent), which can cooperate with the mouth section to obtain a large opening. More importantly, the guide section can get closer to the inner wall of the stent in the closed configuration to avoid local blood accumulation and formation of thrombus.

Optionally, V1 is 4 to 20 times of V2.

Optionally, in the closed configuration, the span of the mouth section in the radial direction of the stent is at least ⅔ times of the diameter of the stent at the leaflets.

The mouth section has a sufficient length in the radial direction to ensure a large opening area.

Optionally, the flap is located at the junction of the mouth section and the guide section.

The flap can also be regarded as a portion which suddenly changes in the extension trend of the movable edge. One side of the flap is the mouth section, which will cause a sudden change of the area of the blood flow channel when opening or closing, and increase the response speed. The other side of the flap is the guide section to promote the corresponding portion of the leaflet to get close to the stent as much as possible in the closed configuration.

Optionally, in the flattened configuration of the leaflet, along the centerline of the movable edge, the distance between the flap and the apex of the movable edge is 1/10 to 1/2 times of the span of the movable edge.

The proper position of the flap ensures the sealing performance of the movable edge. In general, if the distance of the flap to the apex of the movable edge in the direction of the centerline of the movable edge is shorter than the distance of the flap to the end of the movable edge, the effect of closing and locking can be effectively ensured.

Optionally, in the closed configuration, the movable edge extends in a two-dimensional plane.

In the prior art, in order to increase the area of the opening of the movable edges, the length of the movable edge is increased, which is greater than the radial span of the movable edge after being closed. Therefore, after being closed, the movable edges will bend back and forth, that is, the movable edges extend in a three-dimensional space. In this disclosure, the steep guide section can ensure sufficient opening area and avoid the formation of bends in a three-dimensional space at the mouth section.

Optionally, in the closed configuration, the projection of the movable edge along the axial direction of the stent is a straight line segment.

Optionally, the intersection line of the movable edges of the two leaflets in the closed configuration passes through the axis of the stent or is offset from the axis of the stent.

In the case where the two leaflets are symmetrically distributed, the intersection line of the movable edges of the two leaflets in the closed configuration passes through the axis of the stent. In the case where the two leaflets have different shapes or sizes, that is, in the case where the two leaflets are distributed asymmetrically, the intersection line of the movable edges of the two leaflets in the closed configuration is offset from the axis of the stent.

Optionally, in the flattened configuration of the leaflet, the mouth section extends along a straight line, or the middle portion of the mouth section protrudes away from the apex of the fixed edge, or protrudes towards the apex of the fixed edge; and the middle portions of the mouth sections of the two leaflets protrude in the same or different directions.

Optionally, in the closed configuration, the mouth sections of the two leaflets overlap with each other fully or partially.

Optionally, the mouth section and the guide section are transitionally connected by an area the edge of which is S-shaped and the S-shaped edge includes a first arc and second arc that are connected to each other and face oppositely.

The first arc is connected to the guide section, the area enclosed by the first arc is the flap, and the apex of the first arc is the apex of the flap.

The second arc is connected with the mouth section, and the apex of the second arc is the end of the mouth section.

Optionally, in the flattened configuration of the leaflet, the distance between the apex of the flap and the end of the mouth section in the direction of the centerline of the leaflet ranges from 0.5 to 0.7 mm.

A flap with a suitable shape can play its full role. The apex of the second arc generally faces outwardly along the radial direction of the stent, which can further increase the radial span of the mouth section, and the S-shaped configuration appropriately increases the width of the portion of the leaflet corresponding to the guide section to improve the guiding and anti-thrombotic effect.

Optionally, the first arc and the second arc are respective segments of a circle or an ellipse, and the radius of the circle ranges from 0.2 to 0.8 mm, and the semi-major axis of the ellipse ranges from 0.2 to 0.8 mm.

The shape of the arc, especially the shape of the first arc, corresponds to the shape of the profile of the flap. The present disclosure optimizes the range of the shape and size of the arc. The flap and the end of the mouth section coordinate with each other in shape, to ensure the opening area of the mouth section and the closing and guiding effect of the flap.

Optionally, the apex of the flap directs towards the centerline of the leaflet.

Optionally, in the open configuration, the mouth sections of the movable edges of the two leaflets are completely separated from each other.

Optionally, in the closed configuration, the movable edge extends from the apex of the movable edge towards the downstream of the blood flow on both sides, and extends away from the apex of the movable edge along the radial direction of the stent.

Optionally, the length of the guide section in the axial direction of the stent is 1/3 to 3 times of the diameter of the stent.

The guide section should be long enough to obtain a sufficient radial deformation to attach to the inside of the stent to avoid thrombus. The diameter of the stent can be adjusted according to the diameter of the venous blood vessel, so the axial length of the guide section and the diameter of the stent have corresponding proportional relationship.

Optionally, the leaflet includes a middle portion corresponding to the mouth section and side portions corresponding to the guide sections, wherein in the closed configuration, the side portion extends towards and get closer to the inner wall of the stent.

The side portions get close to the inner wall of the stent, which can force out the blood between the side portion and the inner wall of the stent to the greatest extent when the leaflets are closed, so as to avoid the formation of thrombus.

Optionally, in the closed configuration, the span of the movable edge in the axial direction of the stent is greater than 0.5 times of the diameter of the stent at the leaflets, more preferably, 0.6 to 3 times.

Optionally, the cross-sectional area of the blood flow channel in the open configuration is at least 70% of the cross-sectional area of the stent at the leaflets.

Optionally, the inner wall of the stent is further provided with a covering film.

The covering film can provide a blood flow channel and improve the flow control effect of the leaflets. The covering film itself may be made of existing materials, which may be the same or different from the material of the leaflet.

Optionally, the covering film is cylindrical and located at the upstream of the leaflets, and the end of the covering film facing the leaflets is connected to the fixed edges of the leaflets to form the blood flow channel.

Optionally, a plurality of cutting areas is provided at intervals at the edge of the end of the covering film away from the leaflets.

The stent can be radially compressed more easily by cutting out a part of area. Further preferably, the cutting area is triangular, trapezoidal, semicircular, or the like.

Optionally, the two leaflets have different radial spans, wherein the leaflet with the larger radial span is the large leaflet, and the leaflet with the smaller radial span is the small leaflet, and the intersection line of the movable edges of the two leaflets in the closed configuration is offset from the axis of the stent.

In the closed configuration, the projection of the intersection line of the movable edges of the two leaflets along the axial direction of the stent is shaped as a straight line segment, and the extension direction of the radial span is perpendicular to the straight line segment.

Optionally, in the closed configuration, the ratio of the area of the projection of the small leaflet and the area of the projection of the large leaflet along the axis of the stent ranges from 0.15:1 to 0.8:1.

Optionally, in the closed configuration, the ratio of the radial span of the small leaflet to the radial span of the large leaflet ranges from 0.2:1 to 0.9:1.

Optionally, in the closed configuration, the ratio of the radial span of the small leaflet to the radial span of the large leaflet ranges from 0.3:1 to 0.6:1.

Optionally, the projection of the intersection line of the movable edges of the two leaflets in the closed configuration along the axial direction of the stent is shaped as a straight line segment, and the straight line segment and the diameter of the stent satisfy: $0.6\ D \leq F < 1\ D$;

Wherein F is the length of the straight line segment, D is the diameter of the stent, and the axial position corresponding to the diameter is the same as the axial positions of the ends of the straight line segment.

Optionally, the straight line segment and the diameter of the stent satisfy: $0.7\ D \leq F \leq 0.95\ D$.

Optionally, the two leaflets have different axial spans along the axis of the stent.

Optionally, in the flattened configuration of the leaflet, the middle portion of the fixed edge protrudes away from the movable edge, and the apex of the protruding portion at the middle portion of the fixed edge is the apex of the fixed edge, and the projections of the apexes of the fixed edges of the leaflets on the axis of the stent are offset from each other.

Optionally, the ratio of the axial span of the small leaflet to the axial span of the large leaflet ranges from 0.4:1 to 0.95:1.

Optionally, the ratio of the axial span of the small leaflet to the axial span of the large leaflet ranges from 0.6:1 to 0.8:1.

Optionally, the two leaflets have different radial spans, wherein the leaflet with the larger radial span is the large leaflet, and the leaflet with the smaller radial span is the small leaflet, and the intersection line of the movable edges of the two leaflets in the closed configuration is offset from the axis of the stent; and in the closed configuration, the projection of the intersection line of the movable edges of the two leaflets along the axial direction of the stent is shaped as a straight line segment, and the extension direction of the radial span is perpendicular to the straight line segment.

Along the direction of the normal blood flow in practice, the apex of the fixed edge of the large leaflet is located at the upstream, and the apex of the fixed edge of the small leaflet is located at the downstream.

Optionally, the distance between the projections of the apexes of the fixed edges of the two leaflets on the axis of the stent is K, the diameter of the stent is D, and the ratio of K to D ranges from ¼ to ⅓.

The stent in the prior art is formed by intersected supporting bars. When fixing the leaflets, the fixed edge is stitched to the corresponding supporting bars by sutures. There are high professional requirements for controlling the positions and the uniformity of the stitches. In addition, it is frequently required to correct the relative position of the leaflets on the stent during the stitching process, which increases the difficulty of operation.

The stent itself has gaps between adjacent supporting bars, but the arrangement of the gaps is related to the arrangement of the supporting bars and the shape of the grid. In general, the gap is large. Although sutures can be passed through the gaps, the positions of the sutures are not fixed.

Optionally, the stent is provided with threading holes for connecting the fixed edges of the leaflets.

In this disclosure, the diameter of the threading hole is relatively small, and the suture would be hard to move after passing through the threading hole. The threading hole can be provided using the width of the supporting bar and be processed within the width. More importantly, the arrangement of the threading holes corresponds to the extension direction of the fixed edge. The fixed edge can be stitched point by point along the extension direction of the threading holes, which can greatly reduce the difficulty of operation, improve the processing efficiency, and reduce the defective rate.

Optionally, the stent is provided with two V-shaped fixing strips, and the threading holes are distributed at corresponding positions of the fixing strips.

The apex of the V-shape fixing strip directs to the downstream of the direction of normal blood flow in practice, and the two sides of the fixed edge of the same leaflet are stitched on different fixed strips.

Optionally, the V-shaped fixing strip includes two fixed rods.

In the flattened configuration of the stent, the two fixed rods are oblique to each other, and the two fixed rods of the same fixing strip respectively correspond to different leaflets.

Optionally, the two fixed rods intersect at the apex of the V-shaped fixing strip or respectively extend to the neighbouring of the apex of the V-shaped fixing strip.

Optionally, in the flattened configuration of the stent, the fixed rods are arranged obliquely to the axis of the stent.

Optionally, the stent is formed by a plurality of intersected supporting bars, wherein some of the supporting bars are locally widened, and the fixed rod is formed at the widened portion; the threading holes are divided into several sets, and the same set of threading holes are arranged on one of the fixed rods.

It is difficult to keep the extension direction of a single supporting bar to be completely consistent with the extension direction of the fixed edge. Therefore, for the fixed edge of the same leaflet, the corresponding threading holes can be divided into several sets connected in sequence. The same set of threading holes is distributed on different supporting bars in accordance with the corresponding relationship with the fixed edge. The supporting bar, the extension direction of which has no sudden change or obvious turning, can be regarded as the same supporting bar.

Optionally, the supporting bar is widened at least at a portion where the threading hole is provided.

Optionally, the fixed rod extends with a consistent width.

Optionally, the width of the widened portion of the supporting bar ranges from 2 to 5 mm.

Since the threading hole needs to have a certain diameter for the needle and suture to pass through, the width of the corresponding portion of the supporting bar where the threading holes are provided may be provided as required.

The diameter of the threading hole itself may be provided according to the commonly used needle and suture.

Optionally, the threading hole is a round hole or an elliptical hole.

The threading holes have a smooth edge to facilitate the threading process. The threading holes of the same supporting bar can be evenly spaced and can also be adjusted according to the extension direction of the fixed edge.

Optionally, the stent has a grid structure, and the same set of threading holes extend for 2 to 6 grids.

Optionally, the two V-shaped fixing strips are arranged at intervals in the circumferential direction of the stent.

Optionally, the two V-shaped fixed strips are symmetrically distributed on both sides of the axis of the stent.

Optionally, the connection line between the apexes of the two V-shaped fixing strips is designated as a reference line, and the reference line is offset from the axis of the stent viewed from the perspective along the axial direction of the stent.

Optionally, the reference line and the diameter of the stent satisfy: $0.6\ D \leq E < 1\ D$;

Wherein E is the length of the reference line, D is the diameter of the stent, and the axial position corresponding to the diameter is the same as the axial position of the apex of the V-shaped fixing strip.

Optionally, the reference line and the diameter of the stent satisfy: $0.7\ D \leq E \leq 0.95\ D$.

Optionally, the two fixed rods of the same fixing strip are not equal in length.

Optionally, in the flattened configuration of the stent, the angles between the two fixed rods of the same fixing strip and the axial direction of the stent are different.

Optionally, the two fixed rods of the same fixing strip extend substantially along a straight line, and the angle between the two fixed rods is greater than 0 degree and less than or equal to 60 degrees.

The venous valve replacement device of the present disclosure improves the sealing performance by adding flaps on the movable edge, and further expands the opening area through the shape of the movable edges to ensure smooth blood flow, and also avoids the formation of local thrombus, and improves safety.

BRIEF DESCRIPTION OF THE DRAWINGS

FIGS. 9a and 9b are respective schematic views of the intersection lines of movable edges in closed configurations in different embodiments;

FIG. 10 is a schematic view of the leaflet according to one embodiment in a flattened configuration;

FIGS. 11a to 11d are respective schematic views of the two leaflets being flattened and overlapped in different embodiments;

DESCRIPTION OF THE EMBODIMENTS

Figure 1:
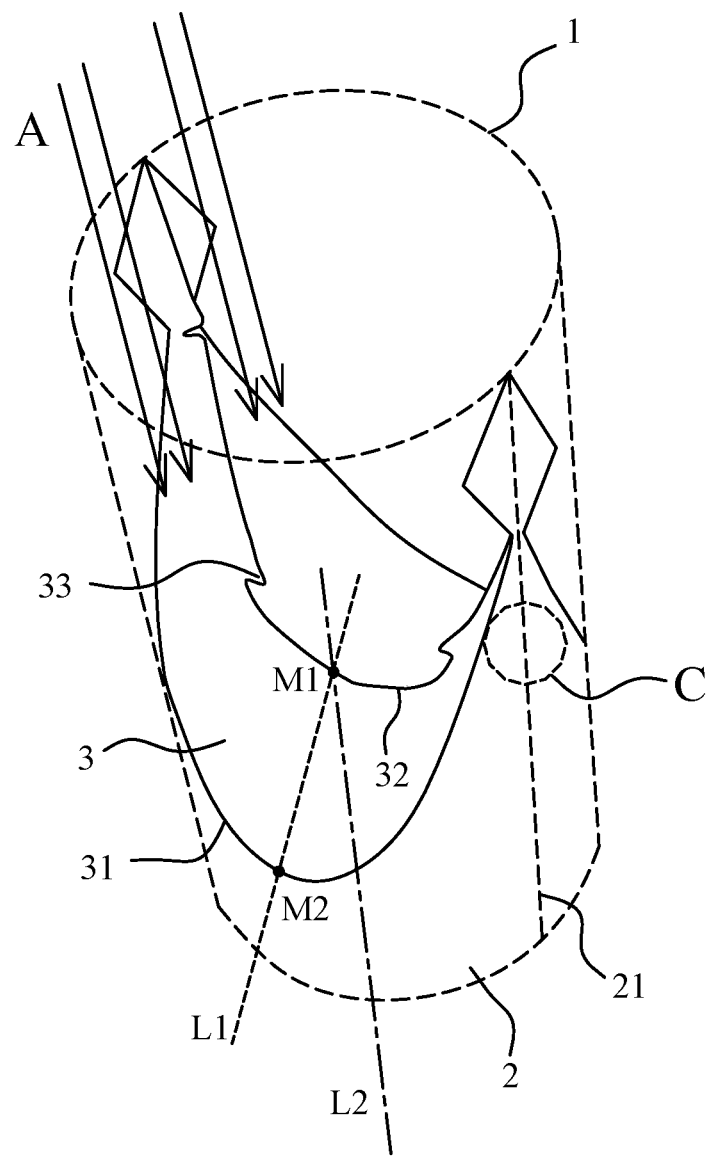
FIG. 1 is a schematic view of the venous valve replacement device of the present disclosure in a closed configuration, in which the stent is not shown and the relative position thereof is indicated by a dashed box.
Figure 2:
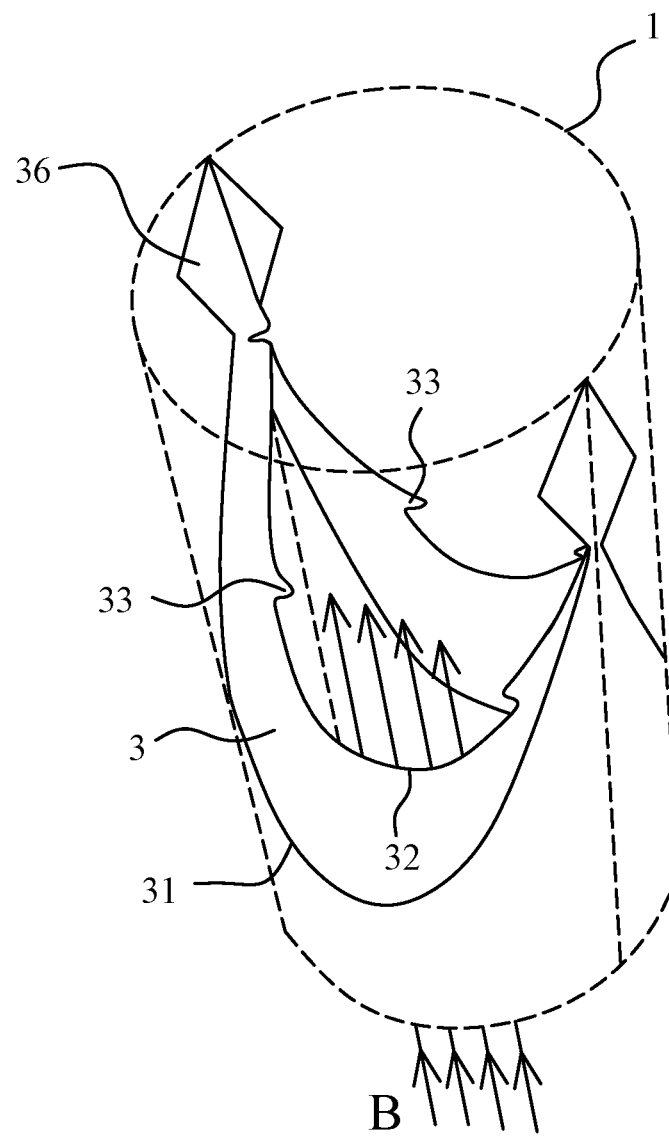
FIG. 2 is a schematic view of the venous valve replacement device in FIG. 1 in an open configuration.

The technical solutions in the embodiments of the present disclosure will be clearly and completely described below in conjunction with the accompanying drawings in the embodiments of the present disclosure. Obviously, the described embodiments are only a part of the embodiments of the present disclosure, not all of the embodiments. Based on the embodiments of the present disclosure, all other embodiments obtained by those skilled in the art without inventive work shall fall within the protection scope of the present disclosure.

One or more drawings may be referred to better describe and illustrate the embodiments of this disclosure. However, the additional details or examples for describing the drawings should not be considered as any limitation to the scope of any one of the invention of the present disclosure, the embodiments or preferred implementations described herein.

It should be noted that when a component is "connected" with another component, it may be directly connected to the other component or may be indirectly connected to another component through a further component. When a component is "provided" on another component, it may be directly provided on another component or may be provided on another component through a further component.

Unless otherwise defined, all technical and scientific terms used herein have the same meaning as commonly understood by those skilled in the art. The terms used in the specification of the present disclosure herein is only for the purpose of describing specific embodiments, not for limiting the present disclosure. The term "and/or" as used herein includes any and all combinations of one or more related listed items.

Referring to FIG. 1 to FIG. 4, in one embodiment of the present disclosure, a venous valve replacement device is provided, which includes a stent 1 with a blood flow channel and two leaflets 3 connected to the stent 1. One side of each leaflet 3 is configured as a fixed edge 31 connected to the stent 1, and the other side is configured as a movable edge 32, wherein the movable edges 32 of the two leaflets 3 cooperates with each other to open or close the blood flow channel. The two leaflets 3 are provided with flaps at the movable edges 32 that attach to each other in a closed configuration.

Even if the leaflets are flattened, the flaps shown in different embodiments of the present disclosure always protrude from the edge of the movable edge, whether or not in folded configurations or viewed from a specific angle.

The stent 1 is generally configured as a meshed tube, which is formed by weaving or cutting and can be compressed radially, so that it can be loaded into a delivery device. The stent 1 is configured to be delivered to a designated position of a venous blood vessel in an interventional manner, and then released. The stent 1 supports the inner wall of the venous blood vessel and the interior thereof functions as a blood flow channel.

The stent 1 is provided with two leaflets 3. One side of each leaflet is configured as a fixed edge 31 connected to the stent 1. The fixed edge 31 is approximately parabolic. The fixed edge 31 is fixed inside the stent by stitching.

In other embodiments, the stent 1 may be simplified. For example, the stent 1 may only include an annular element supporting the inner wall of the venous blood vessel, and a support frame connected to the annular element, wherein the support frame may be shaped to adapt to the shape of the fixed edges of the two leaflets. The annular element may extend for a certain distance in the axial direction, and the extension distance corresponds to the axial dimension of the covering film 2. Alternatively, the support frame of the stent may be indirectly connected to the annular element via a connecting rod.

The other sides of the leaflets are configured as movable edges 32 that cooperate with each other to open or close the blood flow channel. Normally, venous blood flows in the direction of arrow B. The movable edges of the two leaflets separates from each other under the action of blood flow, that is, the blood flow channel is opened. When the venous blood flows back, the two leaflets are closed under the action of the back-flow blood in the direction of arrow A, and the two movable edges are attached to each other to prevent the venous blood from further flowing back.

Depending on the sealing requirement, in another embodiment, the inner side of the stent 1 may be further provided with a covering film 2. The top edge of the covering film 2 is connected with the fixed edge 31 of the leaflet 3. The bottom edge of the covering film 2 is provided with a plurality of triangular cutting areas. The covering film 2 is enclosed in a cylindrical shape, and the junctions thereof are stitched together at a seam 21.

The flap 33 and its corresponding leaflet 3 may be formed in one or separate pieces. The two leaflets may be formed in one or separate pieces.

In a preferred embodiment, the flap 33 protrudes from the corresponding movable edge 32. The flaps on the two leaflets can overlap with each other to increase the contact area and ensure the sealing performance.

In the present disclosure, the shape of the leaflet 3 is further improved. In one embodiment, in a flattened configuration of the leaflet 3, the middle of the fixed edge 31 protrudes away from the movable edge, and the apex of the protruding portion at the middle of the fixed edge is designated as the apex M2 of the fixed edge; the middle of the movable edge protrudes towards the fixed edge, and the apex of the protruding portion is designated as the apex M1 of the movable edge.

In practice, the overall shape of the fixed edge is parabolic. The apex of the fixed edge is located at the upstream of the blood flow, and the fixed edge gradually extends towards the downstream of the blood flow from the apex of the fixed edge on both sides. In order to prevent the blood from flowing back, the fixed edge is connected to the stent in a sealing manner.

In a preferred embodiment, each single leaflet 3 is formed in a substantially symmetrical structure. For example, the line connecting the apex M1 of the movable edge and the apex M2 of the fixed edge is designated as the centerline L1 of the leaflet, and the leaflet 3 is generally symmetrical relative to the centerline L1 of the leaflet.

In one embodiment, in the closed configuration, the angle between the centerline L1 of the leaflet and the axis L2 of the stent ranges from 30 to 60 degrees. In a preferred embodiment, the angle between the centerline L1 of the leaflet and the axis L2 of the stent ranges from 30 to 45 degrees. In the closed configuration, the angle between the centerline L1 of the leaflet and the axis L2 of the stent generally reflects the angle between the two leaflets in the closed configuration, and the angle affects the flexibility of the leaflets to open or close.

In the closed configuration, the movable edge 32 extends from the apex of the movable edge towards the downstream of the blood flow on both sides, and extends away from the apex of the movable edge along the radial direction of the stent. In one embodiment, in order to ensure that the opening of the leaflets has enough area, the span of the movable edge 32 in the axial direction of the stent is greater than 0.5 times of the diameter of the stent at the leaflets.

Each leaflet may be provided with multiple flaps, such as 2 to 4 flaps, which are generally divided into two sets respectively on both sides of the centerline L1 of the leaflet.

In one embodiment, each leaflet is provided with two flaps 33, with one flap 33 provided on each side of the centerline L1 of the leaflet.

In a preferred embodiment, the two flaps 33 are symmetrically distributed with respect to the centerline L1 of the leaflet.

The cooperated flaps on the two leaflets are not strictly limited in size or to be the same, provided that at least parts of the flaps can be overlapped with and attached to each other in the closed configuration. In a preferred embodiment, the flaps on the two leaflets have the same structure and correspond to each other in the closed configuration. "The flaps have the same structure" may be interpreted that the flaps match each other in shape and size. In an ideal overlapped configuration, the edges of the two flaps are aligned with each other. Considering the processing and stitching errors, the flaps in this embodiment are not strictly limited to be the same. For example, 80% of the area of one of the flaps is attached with the other corresponding flap.

The position of the flap 33 relative to the centerline of the movable edge has a certain impact on the opening flexibility and the closing effect. In one embodiment, in the flattened configuration of the leaflet, relative to the centerline of the movable edge, the distance of the flap 33 and the apex of the movable edge is 1/10 to 1/2 times of the span of the movable edge. That is, in the overall span of the movable edge, the flap 33 is closer to the apex of the movable edge.

Since the closer the movable edge relative to the fixed edge, the narrower the size of the leaflet, in one embodiment, the movable edge 32 and the fixed edge 31 on the same side of the centerline L1 of the leaflet are gradually closer to each other and connected by a patch 36 which is fixed to the stent 1, which facilitates the stitching process and maintains the relative position between the leaflet and the stent.

The movable edge 32 may extend from the flap 33 along a smooth curve to the neighbouring of the inner side of the stent 1. However, in order to improve the opening or closing flexibility of the leaflet at the movable edge 32, in one embodiment, the movable edge 32 is provided with a notch 37 adjacent to the patch 36 to increase the relative degree of freedom of the leaflet. In a preferred embodiment, in order to avoid local stress concentration, the profile of the notch 37 is configured as a smooth curve. The notch 37 can reduce the restriction of the movable edge 32 by the patch 36, thereby improving and increasing the flexibility of the movable edge 32 to open or close.

In order to further divide and easily describe the structure of the movable edge 32, in one embodiment, the movable edge 32 includes a mouth section 34 located near the apex M1 of the movable edge, and guide sections 35 located on both sides of the mouth section 34.

Figure 3:
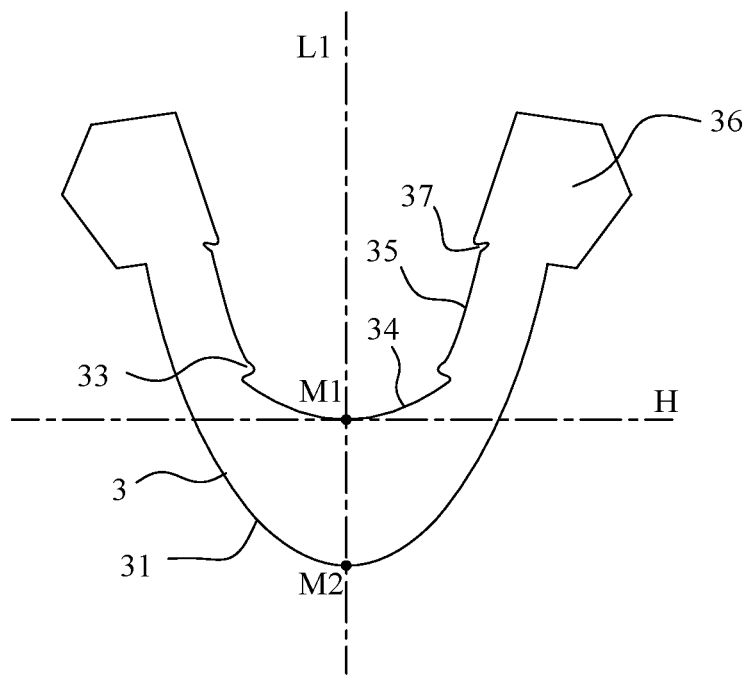
FIG. 3 is a schematic view of the leaflets of the venous valve replacement device of the present disclosure, with the leaflets flattened.
Figure 4:
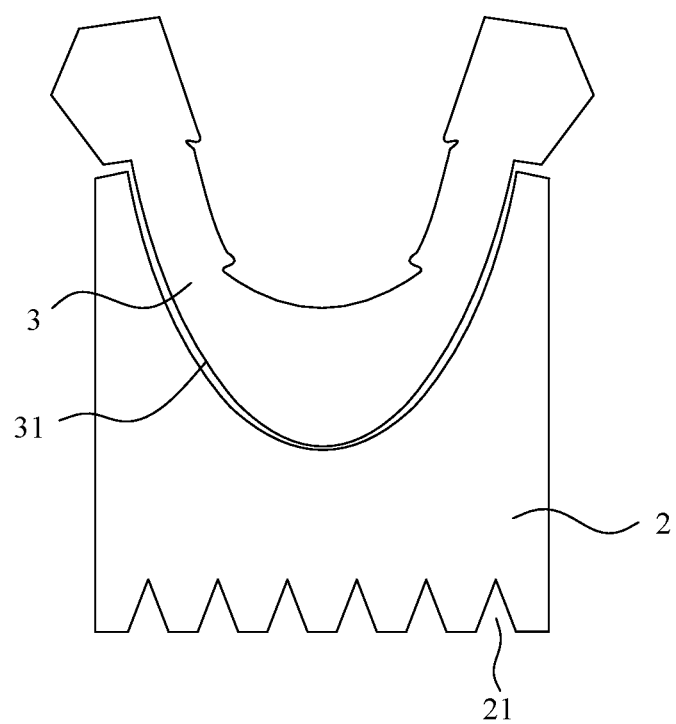
FIG. 4 is a schematic view of the leaflet shown in FIG. 3 in combination with a covering film for the stent.

It can be seen from FIG. 3 that relative to the vertical line H of the centerline L1 of the leaflet, the mouth section 34 is relatively flat, which can improve the speed and flexibility of opening or closing, and the guide sections 35 on both sides are relatively steep, which can cooperated with the mouth section 34 to form a larger opening, and can be closer to the inner wall of the stent in the closed configuration, thereby avoiding the accumulation of blood in the area C between the top of the guide section and the stent and thus the formation of thrombus.

In order to further compare the extension trend of the mouth section 34 and the guide section 35, the radial outward extending rate of the mouth section 34 is designated as V1, the radial outward extending rate of the guide section 35 is designated as V2, and V1 is greater than V2. For example, in different embodiments, V1 may be 4 to 20 times of V2.

The term of the radial outward extending rate is defined as the variation of the radial position when extending for a unit distance along the axial direction of the stent. The larger the radial outward extending rate, the greater the radial extending component, and the flatter the overall extending trend.

The guide section 35 should be long enough to obtain a sufficient radial deformation to attach to the inside of the stent to avoid thrombus. In one embodiment, the length of the guide section 35 in the axial direction of the stent is 1/3 to 3 times of the diameter of the stent.

The mouth section 43 has a sufficient length in the radial direction to ensure a large opening area. In the closed configuration, in one embodiment, the mouth section 34 spans at least 2/3 times of the diameter of the stent at the leaflets.

In a preferred embodiment, in the opened configuration, the mouth sections 34 of the two leaflets are completely separated, and the cross-sectional area of the blood flow channel is more than 80%, at least 70%, of the cross-sectional area of the stent at the leaflets.

The periphery of the blood flow channel is surrounded by movable edges. In order to provide sufficient cross-sectional area for the blood flow channel, the movable edges of the two leaflets should have sufficient length in their respective extension direction. When the length of the two leaflets is equal to the circumferential length of the stent, in theory, the cross-sectional area of the blood flow channel can be up to 100% of the cross-sectional area of the stent at the leaflets.

For example, in one embodiment, the length of the movable edge in its own extension direction ranges from 1.4 times of the diameter of the stent to half of the circumferential length of the stent.

Depending on the stitching manner, taking the stent with a consistent diameter as an example, the cross-sectional area of the blood flow channel is generally slightly smaller than the cross-sectional area of the stent.

Figure 5:
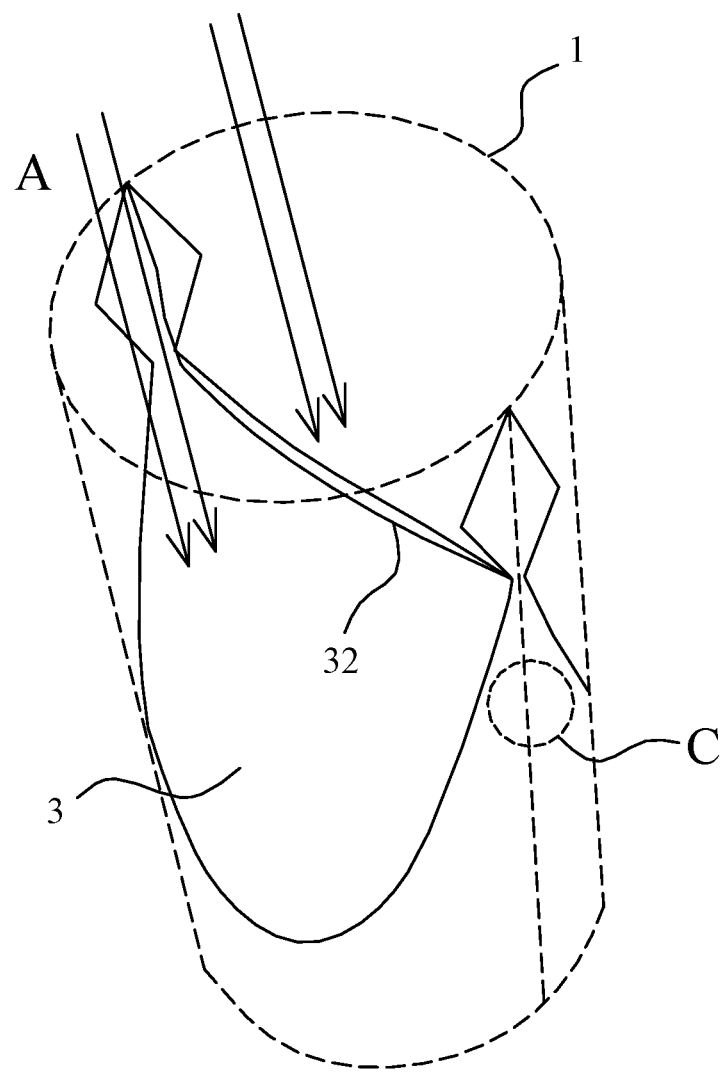
FIG. 5 is a schematic view of a venous valve replacement device according to a comparative example in the closed configuration.
Figure 6:
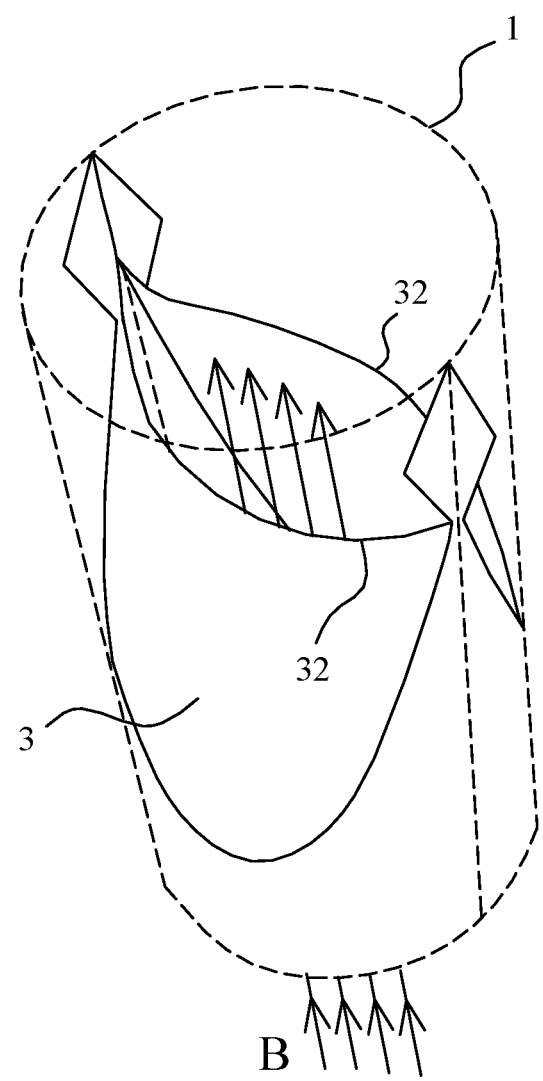
FIG. 6 is a schematic view of the venous valve replacement device in FIG. 5 in an open configuration.
Figure 7:
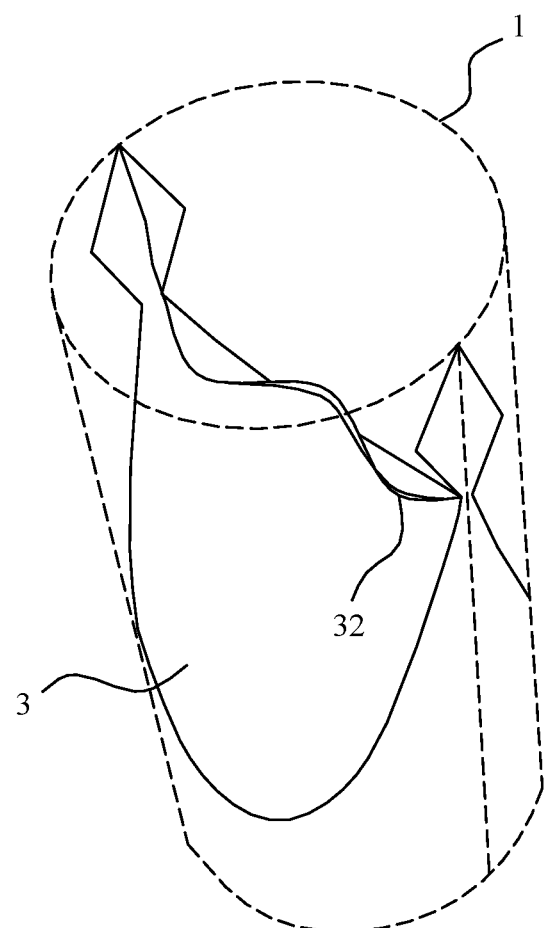
FIG. 7 is a schematic view of a venous valve replacement device according to another comparative example in the closed configuration.

In one embodiment, the diameter of the stent is enlarged at the stitched portions of the leaflets, so that the thickened area by stitching can be avoided as much as possible, thereby ensuring a sufficient cross-sectional area of the blood flow channel. Referring to FIGS. 5 and 6, in some two-leaflet valve structures in the other fields of the prior art, in order to ensure the sealing performance, the movable edges 32 are generally flat so that it is possible to tighten the movable edges 32 to close the blood flow channel. However, after closing the blood flow channel, the area C between the leaflets 3 and the stent 1 at the upstream of the blood flow has a large space, and it is easy to accumulate blood and form a thrombus. In addition, since the movable edges are straightly tightened, it is difficult to form a blood flow channel with a larger cross-sectional area after the leaflets are opened. Referring to FIG. 7, although the movable edges 32 can be lengthened to ensure a sufficient opening area, the movable edges 32 would form one or more bends after being closed, causing the two leaflets to be partially separated and affecting the sealing performance.

In the closed configuration, the movable edges 32 of the venous valve replacement device according to this embodiment are located in the two-dimensional plane.

Referring to FIG. 9a, in a preferred embodiment, the projection of the movable edges in the axial direction of the stent in the closed configuration is shaped in a straight line segment, which avoids a bend presented in the three-dimensional space. In the FIG. 9a, a leaflet 3a and a leaflet 3b is provided in the stent 1. In the closed configuration, the movable edges of the two leaflets are attached to each other to close the blood flow channel, and viewed from the axial direction of the stent, the position where the movable edges are attached to each other is an intersection line 3c of the movable edges. It can be seen from the FIG. 9a that the intersection line 3c of the movable edges is shaped in a straight line segment.

When the leaflet 3a and leaflet 3b have the same shape viewed from the axial direction of the stent, the intersection line 3c of the movable edges in the closed configuration passes through the axis of the stent, so that the intersection line 3c can also be regarded as the diameter of the stent 1.

Referring to FIG. 9b, in other embodiments, in the case where the shapes of the leaflets 3a and 3b are not symmetrical to each other, the intersection line 3c of the movable edges in the closed configuration is offset from the axis of the stent. That is, the intersection line 3c is offset from the diameter D of the stent 1, and is separated by a certain distance from the diameter D of the stent 1.

Figure 8:
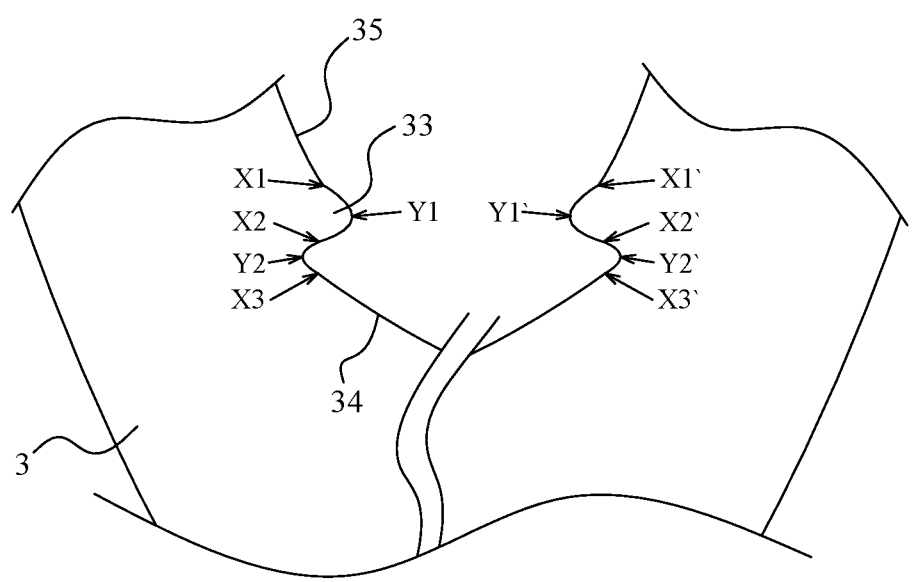
FIG. 8 is a partial schematic view of the leaflet shown in FIG. 3.

Referring to FIG. 8, in the flattened configuration of the leaflet 3, the mouth section 34 and the guide section 35 are connected by an S-shaped edge, and the S-shape transition section includes a first arc and a second arc that are connected to each other and face oppositely;

The first arc and the second arc are not strictly limited to a standard geometric arc, but are merely used to define the overall shape. In some preferred embodiments, the first arc and the second arc are respectively a segment of a circular arc.

The two ends of the first arc are the endpoint X1 and the endpoint X2, the middle portion of the first arc is the apex Y1, and the apex Y1 faces the centerline of the leaflet.

The two ends of the second arc are the endpoint X2 and the endpoint X3, the middle portion of the second arc is the apex Y2, and the apex Y2 faces away from the centerline of the leaflet.

Two guide sections 35 are respectively distributed on both sides of the centerline of the leaflet. On the other side of the centerline of the leaflet, a corresponding S-shape transition section is also provided, which also includes two arcs that are connected to each other and face oppositely. The first arc has an endpoint X1' and an endpoint X2', the middle portion of the first arc is the apex Y1'. The second arc has an endpoint X2' and an endpoint X3', and the middle portion of the second arc is the apex Y2'.

The left side of the centerline of the leaflet is taken as an example, and the same applies to the right side of the centerline of the leaflet. The first arc is connected with the guide section 35, the area enclosed by the first arc is the flap 33, and the apex Y1' of the first arc is the apex of the flap. The two ends of the first arc are the endpoints X1 and X2 respectively, so the area enclosed by the first arc is the area enclosed by the arc segment of the first arc and the boundary line segment. The two endpoints of the boundary line segment are the endpoints X1 and X2.

The second arc is connected to the mouth section 34, and the apex Y2 of the second arc is designated as the end of the mouth section.

The distance between the apex of the flap and the end of the mouth section in the direction of the centerline of the leaflet ranges from 0.5 to 0.7 mm. The first arc and the second arc are respective segments of a circle or an ellipse. In the case where the first arc and the second arc are circular, the corresponding radius ranges from 0.2 to 0.8 mm. In the case where the first arc and the second arc are elliptical, the corresponding semi-major axis ranges from 0.2 to 0.8 mm.

In one embodiment, the area of the flap ranges from 0.1 to 10 square millimeters, and preferably, from 4 to 6 square millimeters.

In this embodiment, the span of the movable edge in the axial direction of the stent in the closed configuration is greater than 0.5 times of the diameter of the stent at the leaflets. The span of the movable edge in the axial direction of the stent shown in FIG. 5 and FIG. 7 is almost 0. In this embodiment, the extension distance of the movable edge is increased through a large axial span of the movable edge, which allows the mouth sections to sufficiently move away from the centerline of the opened blood flow channel in the opened configuration.

When the venous valve replacement device in this embodiment works, normal venous blood flows in the direction of arrow B, and pressure from the blood flow is applied to the two leaflets. The movable edges of the two valves are separated from each other, and the mouth sections are completely separated from each other.

When venous blood flows back, the back-flow blood flows in the direction of arrow A. When the back-flow blood flows through the guide section to the flaps, the guide sections of the two leaflets are relatively steep and will easily get close to each other under the action of the back-flow blood. In combination with the further guidance of the flaps, the movable edges of the two leaflets will close flexibly. The movable edges are linearly contacted to each other to a certain extent, while the sealing profile is not stable. However, in this embodiment, due to the flaps which contact to each other in surfaces, the movable edges of the two leaflets can be maintained in the closed configuration to ensure the sealing performance.

Referring to FIG. 10, another embodiment differs from the foregoing embodiments in that in the flattened configuration of the leaflet 3, the middle portion of the mouth section 34 protrudes away from the apex of the fixed edge, and the sealing performance is better when the mouth sections 34 are closed.

The apex of the protruding portion is the apex M1 of the movable edge, and the connection line between the apex M1 of the movable edge and the apex M2 of the fixed edge is designated as the centerline L1 of the leaflet. Relative to the vertical line H of the centerline L1 of the leaflet, the mouth section 34 protrudes away from the apex of the fixed edge. Although the mouth section 34 in this embodiment protrudes away from the apex of the fixed edge, the middle portion of the movable edge generally protrudes towards the apex of the fixed edge.

The middle portions of the mouth sections of the two leaflets may protrude in the same or different directions. In the case where the middle portions of the mouth sections of the two leaflets protrude in the same direction, especially in the case where the two leaflets have the same shape, in the closed configuration, the mouth sections of the two leaflets are completely overlapped. For example, both leaflets may adopt the structure shown in FIG. 3, or the structure shown in FIG. 10.

Referring to FIGS. 11a to 11d, in some embodiments, in the case where the shapes of the two leaflets are different, especially in the case where the middle portions of the mouth sections of the two leaflets protrude in the different directions, or to the different extents, the mouth sections of the two leaflets in the closed configuration only partially overlap to each other. The two leaflets shown in FIG. 11a adopt the structures shown in FIGS. 3 and 10 respectively. For the convenience of comparison, the two leaflets are shown in flattened configurations in FIGS. 11a to 11d. Except for the mouth sections, the other portions of the two leaflets generally overlap to each other, and the mouth section 34a of one leaflet protrudes away from the apex of the fixed edge, the mouth section 34b of the other leaflet protrudes towards the apex of the fixed edge. The two mouth sections overlap to each other only at the ends after being attached to each other.

Compared to FIG. 11a, in another embodiment shown in FIG. 11b, although the mouth section 34a protrudes away from the apex of the fixed edge, and the mouth section 34b protrudes toward the apex of the fixed edge, the mouth sections protrude slightly differently and obviously protrude to a lesser extent relative to that shown in FIG. 11a. The two mouth sections overlap to each other only at the ends after being attached to each other, and the area enclosed by the mouth sections is slightly smaller.

Figure 11C:
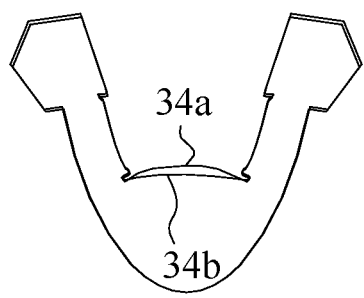

In another embodiment shown in FIG. 11c, the mouth section 34a protrudes away from the apex of the fixed edge, and the mouth section 34b also protrudes away from the apex of the fixed edge. However, the mouth sections 34a and 34b protrude to different extents. The two mouth sections overlap to each other only at the ends after being attached to each other.

Figure 11D:
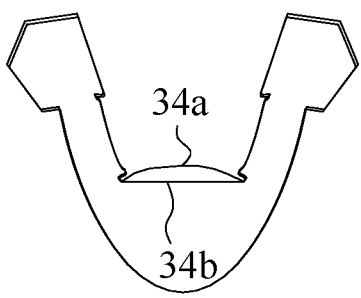

In another embodiment shown in FIG. 11d, the mouth section 34a protrudes away from the apex of the fixed edge, and the mouth section 34b extends substantially along a straight line. The two mouth sections overlap to each other only at the ends after being attached to each other.

Figure 12:
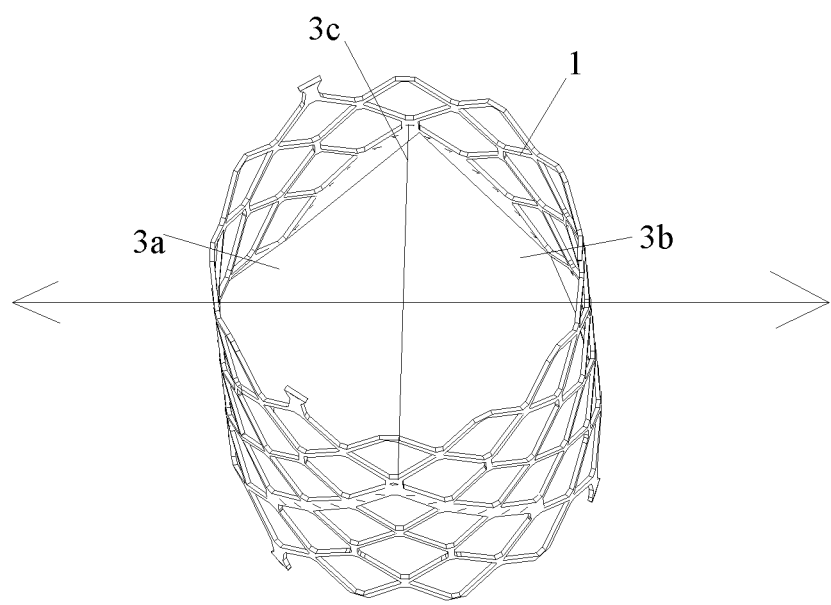
FIG. 12 shows two leaflets according to one embodiment viewed from an axial direction.

Referring to FIG. 12, in one embodiment, the venous valve replacement device includes a stent 1 with a blood flow channel and two leaflets, namely leaflet 3a and leaflet 3b, connected to the stent 1. One side of each leaflet 3a or 3b is configured as a fixed edge connected to the stent 1, and the other side is configured as a movable edge, wherein the movable edges of the two leaflets 3a or 3b cooperates with each other to open or close the blood flow channel. The two leaflets have the same shape and are symmetrically distributed. The intersection line 3c of the movable edges of the two leaflets is generally shaped in a straight line segment viewed from the axial direction of the stent, and the two ends of the intersection line 3c intersect with the stent 1. Since the two leaflets are of the same shape and symmetrically distributed, the intersection line 3c of the movable edges passes through the axis of the stent and can be regarded as a diameter of the stent. Also viewed from the axial direction of the stent, in FIG. 12, the direction with arrows is perpendicular to the intersection line 3c of the mo edge, and the spans of the two leaflets in the direction with arrows is designated as the radial spans, and the leaflet 3a and the leaflet 3b have the same radial span.

Figure 13A:
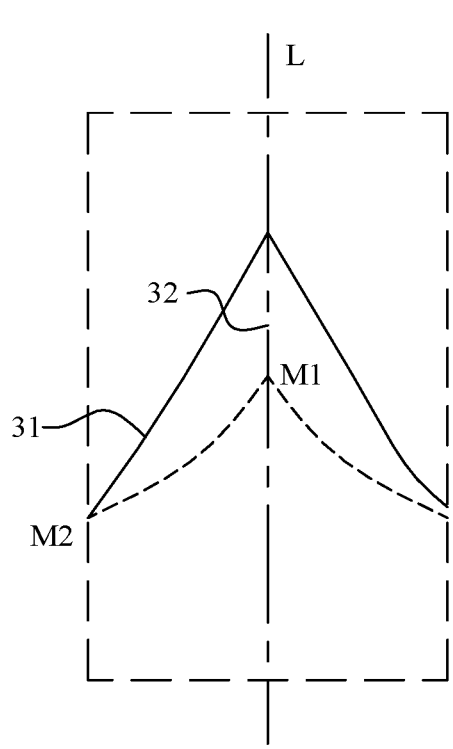
FIGS. 13a and 13b are respective schematic views of the two leaflets in the closed and opened configurations viewed from the direction of the intersection line of the movable edges in the embodiment where the leaflets are symmetrical.
Figure 13B:
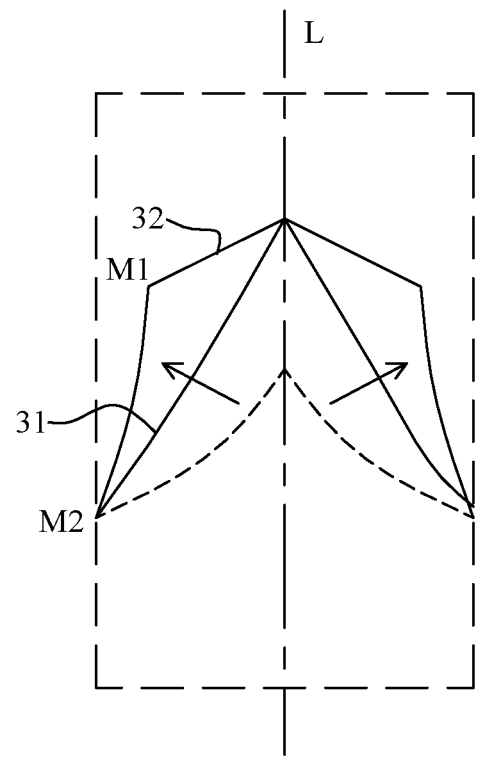

For further clarity, taking one of the leaflets shown in FIG. 12 as an example, and in conjunction with FIG. 12, FIG. 13a, FIG. 13b, viewed from the intersection line 3c of the movable edges, when the leaflet transforms between the opened configuration and the closed configuration, the positions of the fixed edge 31 and the apex M2 of the fixed edge relative to the stent is fixed, while the movable edge 32 in the closed configuration intersects with the axis L of the stent, and the apex M1 of the movable edge is located on the axis L.

Under the action of normal blood flow, when the leaflets are opened, the apex M1 of the movable edge moves away from the axis L and attaches to the inner wall of the stent in the direction of the arrow shown in FIG. 13b. Undoubtedly, the movable edges 32 generally move accordingly, and the movable edges of the two leaflets are relatively open to allow blood to flow, and vice versa when the leaflets are closed.

Referring to FIGS. 14a to 14d, in one embodiment, the venous valve replacement device includes a stent 1 with a blood flow channel and two leaflets connected to the stent 1. One side of each leaflet is configured as a fixed edge connected to the stent 1, and the other side is configured as a movable edge, wherein the movable edges of the two leaflets cooperates with each other to open or close the blood flow channel.

The two leaflets have the different shapes, and at least the radial spans of the two leaflets are different. The leaflet with the larger radial span is designated as the large leaflet, and the leaflet with the smaller radial span is designated as the small leaflet. As shown in FIGS. 14a to 14d, the small leaflet is on the left and has a fixed edge 31a and a movable edge 32a, and the large leaflet is on the right and has a fixed edge 31b and a movable edge 32b.

In the closed configuration, the intersection line 3c of the movable edges of the two leaflets is offset from the axis L of the stent, and the intersection line passes through another straight line L' parallel to the axis L. Based on the asymmetric leaflets, not only an one-way valve for the venous valve with the function of opening or closing can be obtained, but also the opening or closing flexibility can be ensured by the small leaflet, and a blood pocket can be formed through the large leaflet when being closed, thereby delivering the pocketed blood upwardly and layer-by-layer.

Figure 14A:
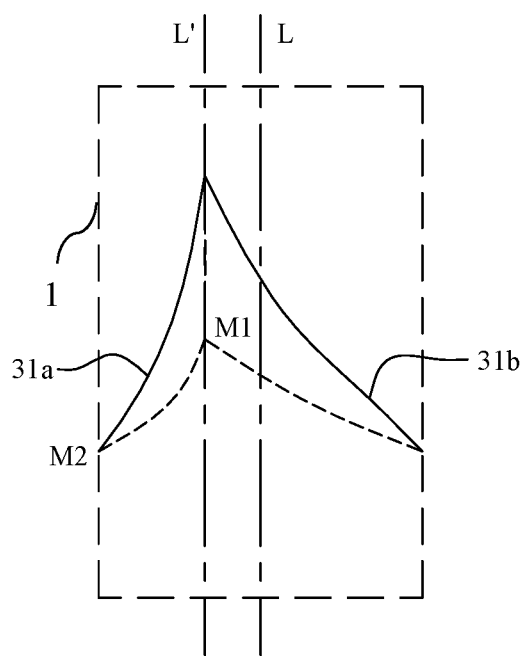
FIGS. 14a to 14d are respective schematic views of the two leaflets in different configurations and from different perspectives in one embodiment where the leaflets are asymmetric.
Figure 14B:
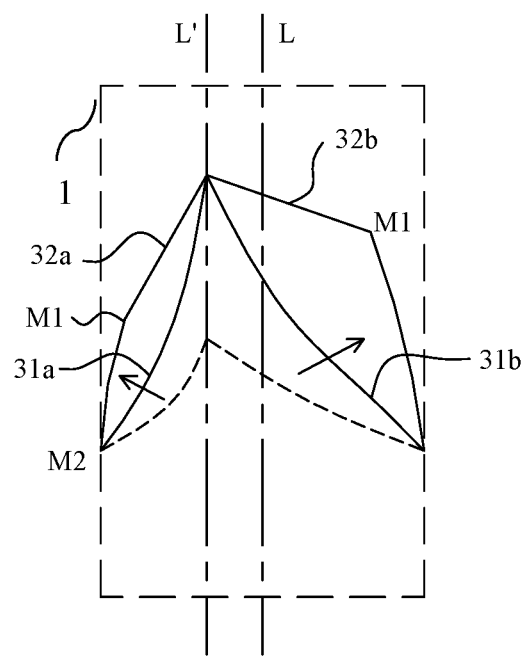
Figure 14C:
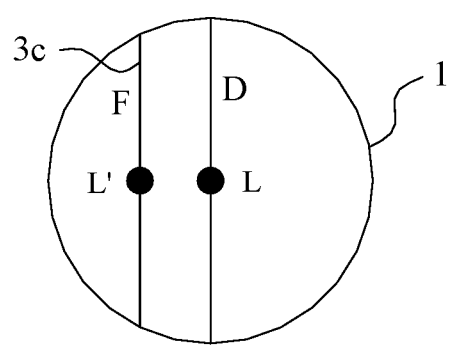

A better performance can be achieved by optimizing the proportion between the small leaflet and the large leaflet. Referring to FIG. 14c, in one embodiment, the projection of the intersection line 3c of the movable edges of the two leaflets in the closed configuration along the axis of the stent is shaped as a straight line segment. The length of the straight line segment is F, and the diameter of the stent 1 is D. In the case where the stent 1 has slightly different diameters in different parts, the diameter of the stent 1 may be interpreted as the diameter of the portion of the stent where the two ends of the intersection line 3c of the movable edges are located. Furthermore, in the case where the two ends of the intersection line 3c of the movable edges have the different axial positions, the intersection line 3 may be interpreted as a line passing through the midpoint of the two ends with different axial positions, and the diameter of the stent D may be interpreted as the diameter of the portion of the stent where the midpoint is located. In this embodiment, it is satisfied: $0.6\ D \leq F < 1\ D$. In other preferred embodiments, $0.7\ D \leq F \leq 0.95\ D$.

Figure 14D:
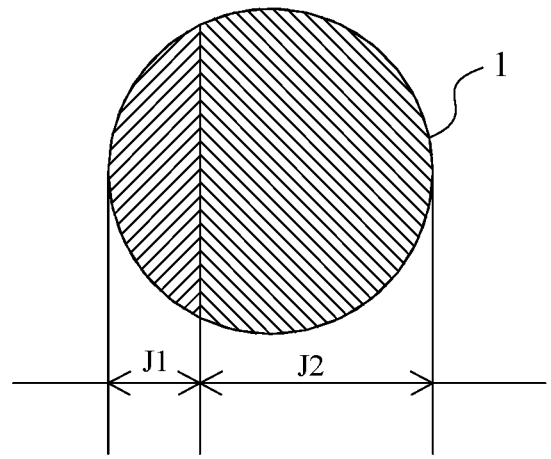

With reference to FIG. 14d, viewed from the axial direction of the stent, in the closed configuration, the ratio of the area of the small leaflet on the left to the area of the large leaflet on the right ranges from 0.15:1 to 0.8:1. In other preferred embodiments, the ratio of the area of the small leaflet on the left to the area of the large leaflet on the right ranges from 0.15:1 to 0.5.1.

Furthermore, the proportion between the small leaflet and the large leaflet may be determined depending on the radial spans of the small leaflet and the large leaflet. The detail for the radial span may be referred to using the description about FIG. 12. In conjunction with FIG. 14d, in one embodiment, the ratio of the radial span J1 of the small leaflet to the radial span J2 of the large leaflet ranges from 0.2:1 to 0.9:1. In other preferred embodiments, the ratio of the radial span J1 of the small leaflet to the radial span J2 of the large leaflet is 0.3 to 0.6:1.

In the case where the two leaflets are asymmetric to each other, regardless of whether the radial spans of the two leaflets are the same, in some embodiments, the axial spans of the two leaflets along the axial direction of the stent may be different to further optimize the opening or closing flexibility.

Figure 15A:
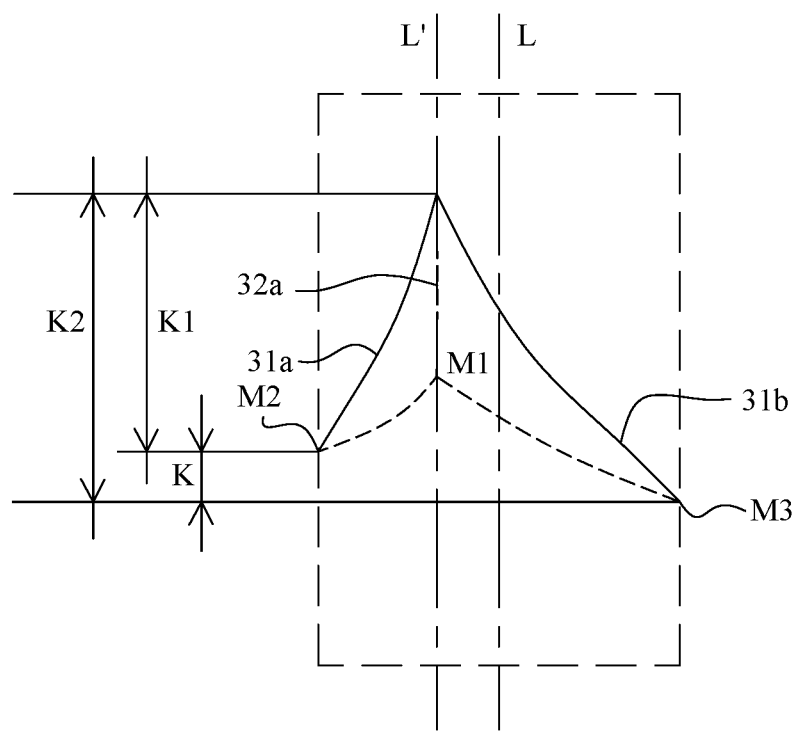
FIGS. 15a and 15b are respective schematic views of the two leaflets in the closed and opened configurations viewed from the direction of the intersecting line of the movable edges in another embodiment where the leaflets are asymmetrical.
Figure 15B:
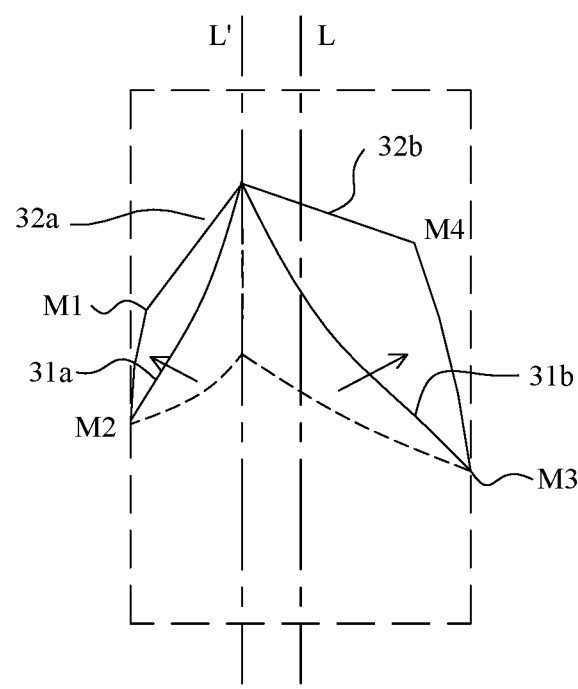

Referring to FIGS. 15a and 15b, in one embodiment, the venous valve replacement device includes a stent with a blood flow channel and two leaflets connected to the stent. One side of each leaflet is configured as a fixed edge connected to the stent, and the other side is configured as a movable edge, wherein the movable edges of the two leaflets cooperates with each other to open or close the blood flow channel.

When the leaflets transform between the opened configuration and the closed configuration, the positions of the fixed edge 31a of the left leaflet and the apex M2 of the fixed edge relative to the stent remain fixed. Under the action of normal blood flow, when the leaflets are opened, the apex M1 of the movable edge will move and attach to the inner wall of the stent along the direction of the arrow shown in FIG. 15b. Undoubtedly, the movable edge 32a generally moves accordingly. The movable edges of the two leaflets are relatively open to allow blood to flow. Similarly, the positions of the fixed edge 31b of the right leaflet and the apex M3 of the fixed edge relative to the stent remain fixed. Under the action of normal blood flow, when the leaflets are opened, the apex M4 of the movable edge will move and attach to the inner wall of the stent along the direction of the arrow shown in FIG. 15b. Undoubtedly, the movable edge 32b generally moves accordingly. The movable edges of the two leaflets are relatively open to allow blood to flow.

The projections of the apex M2 of the fixed edge of the left leaflet and the apex M3 of the fixed edge of the right leaflet on the axis L of the stent are offset from each other (the apex of the fixed edge is located at the most upstream position of the two leaflets along the direction of the normal blood flow), that is, the axial positions of the two are different, while the most downstream positions of the fixed edges of the two leaflets along the direction of the normal blood flow are the same, so that the two leaflets have different axial spans.

As shown in FIG. 15a, the axial span of the left leaflet is K1, and the axial span of the right leaflet is K2. Obviously, K1 is smaller than K2. In one embodiment, the ratio of K1 to K2 ranges from 0.4:1 to 0.95:1. In other preferred embodiments, the ratio of K1 to K2 ranges from 0.6:1 to 0.8:1.

In order to further optimize the axial spans of the two leaflets, in one embodiment, the difference between K1 and K2 is K, the diameter of the stent is D, and the ratio of K to D ranges from ¼ to ⅓.

In the case where the stent has slightly different diameters in different parts, the diameter of the stent may be interpreted as the diameter of the portion of the stent where the axial midpoint of the apex M2 of the fixed edge and the apex M3 of the fixed edge are located.

In some embodiments, the leaflets may have the different axial spans as well as different radial spans, and can also cooperate with each other well. Referring to FIGS. 15a and 15b, the two leaflets in this embodiment have the different radial spans. The leaflet with the larger radial span is designated as the large leaflet, and the leaflet with the smaller radial span is designated as the small leaflet. As shown in FIGS. 15a and 15b, the small leaflet is on the left side and has a fixed edge 31a and a movable edge 32a. The large leaflet is on the right side and has a fixed edge 31b and a movable edge 32b.

The intersection line of the movable edges of the two leaflets in the closed configuration is offset from the axis L of the stent, and the intersection line passes through another straight line L' parallel to the axis L. In the direction of the normal blood flow, the apex M3 of the fixed edge of the large leaflet is located at the upstream, and the apex M2 of the fixed edge of the small leaflet is located at the downstream. That is, both the radial and axial spans of the small leaflet are smaller than those of the large leaflet. The radial spans of the two leaflets in this embodiment can be referred to using the disclosure of FIG. 14d. For example, the ratio of the radial span J1 of the small leaflet to the radial span J2 of the large leaflet ranges from 0.2:1 to 0.9:1. In other preferred embodiments, the ratio of the radial span J1 of the small leaflet to the radial span J2 of the large leaflet ranges from 0.3:1 to 0.6:1.

Referring to FIGS. 16a to 17d, in this embodiment, the stent 1 is formed by cutting, and is generally shaped as a cylinder with a grid structure. At least one of the two ends in the axial direction of the stent is provided with a connecting element 14 for connecting with the delivery device.

In order to facilitate the installation of the leaflets, the stent 1 in this embodiment is provided with threading holes 13 for connecting the fixed edges of the leaflets.

The threading holes 13 facilitate the threading of the suture for stitching the leaflets, and makes the stitches uniform. The density of the threading holes 13 may be provided according to the stitching requirements, and the same threading hole is not limited to be threaded by only once.

The edge of the threading hole 13 is generally required to be relatively smooth. For example, the threading hole may be shaped as a round hole. Alternatively, the threading hole may be shaped as an elliptical hole in other embodiments. The threading hole 13 may be provided by locally processing the structure of the stent itself, or through an additional component, or using the hollow structure of the stent itself.

In one embodiment, the stent 1 is provided with two V-shaped fixed strips, and the threading holes 13 are distributed at corresponding positions of the fixed strips.

For example, in FIGS. 16a to 16d, the V-shaped fixed strip includes two fixed rods, namely the fixed rod 11 and the fixed rod 12, and the two fixed rods are arranged oblique to each other.

Figure 16A:
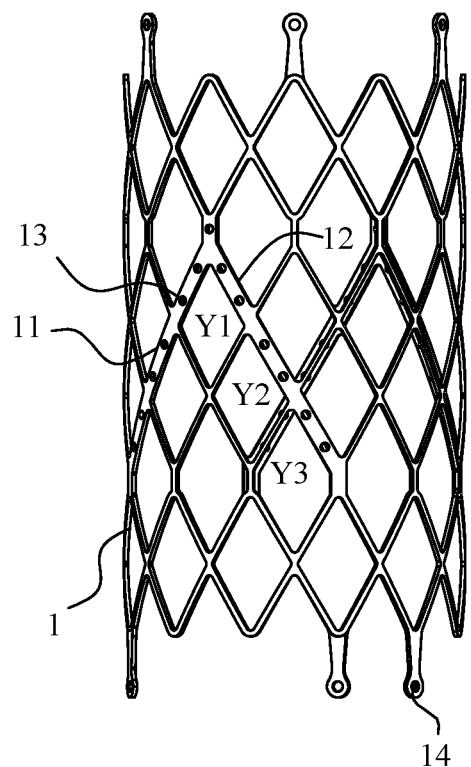
FIGS. 16a to 16d are respective schematic views of the stent in different embodiments from different perspectives.
Figure 16B:
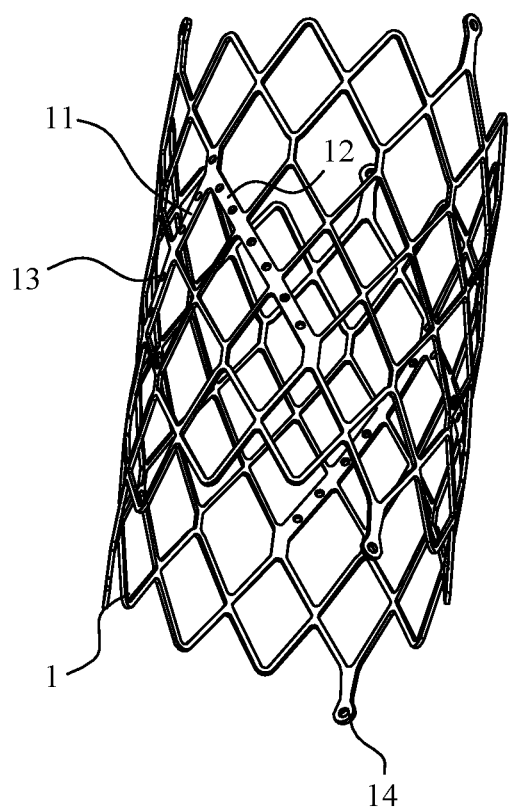
Figure 16C:
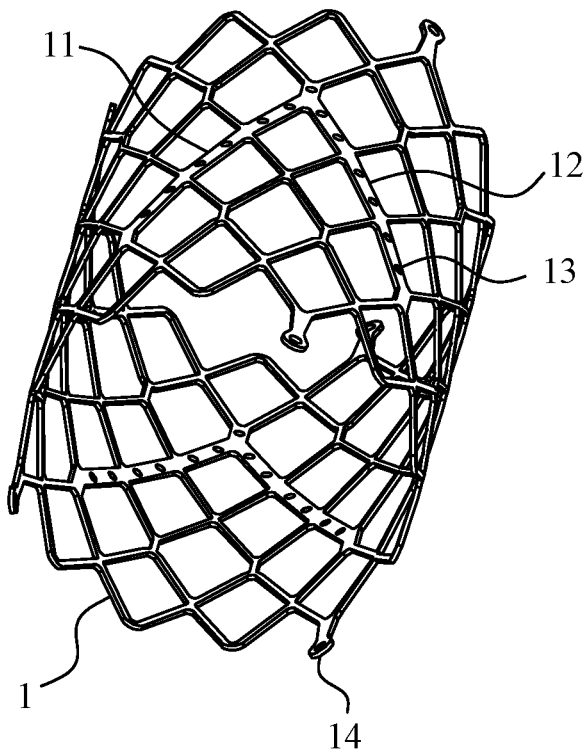
Figure 16D:
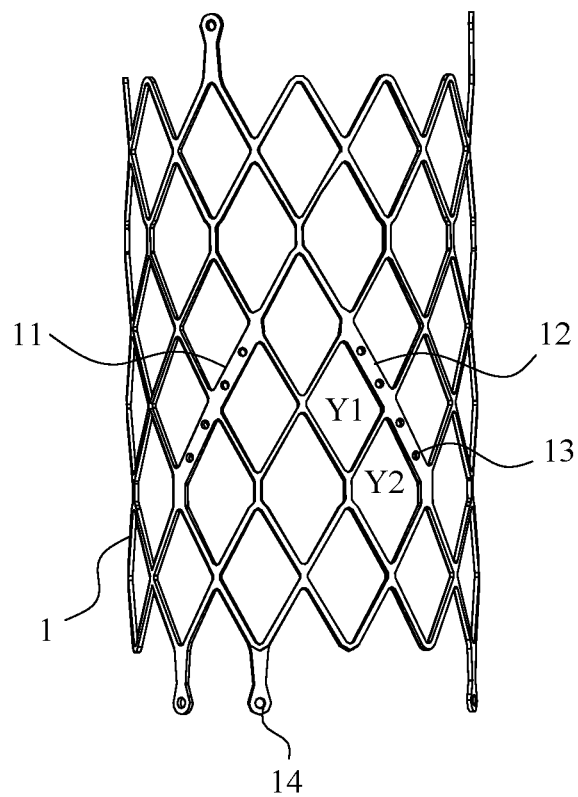
Figure 17A:
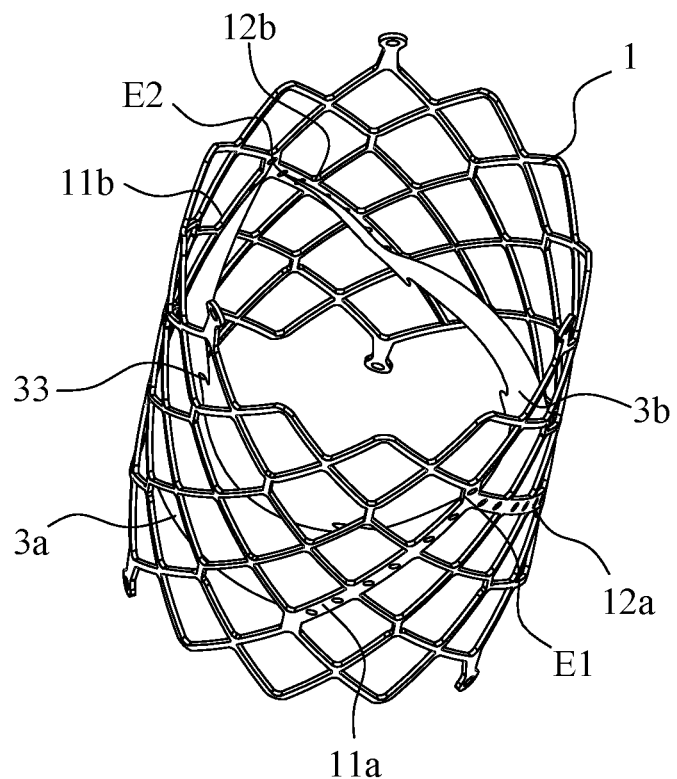
FIGS. 17a to 17d are respective schematic views of the venous valve replacement devices in different embodiments from different perspectives.
Figure 17B:
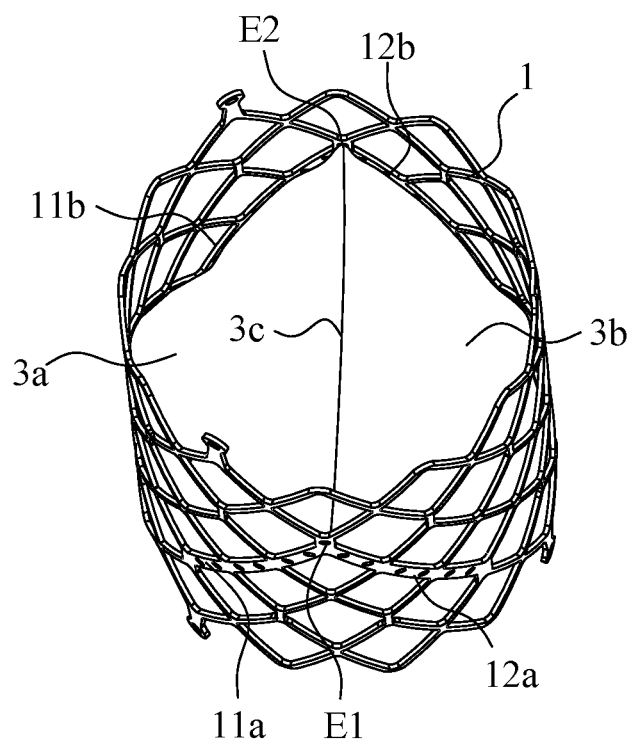
Figure 17C:
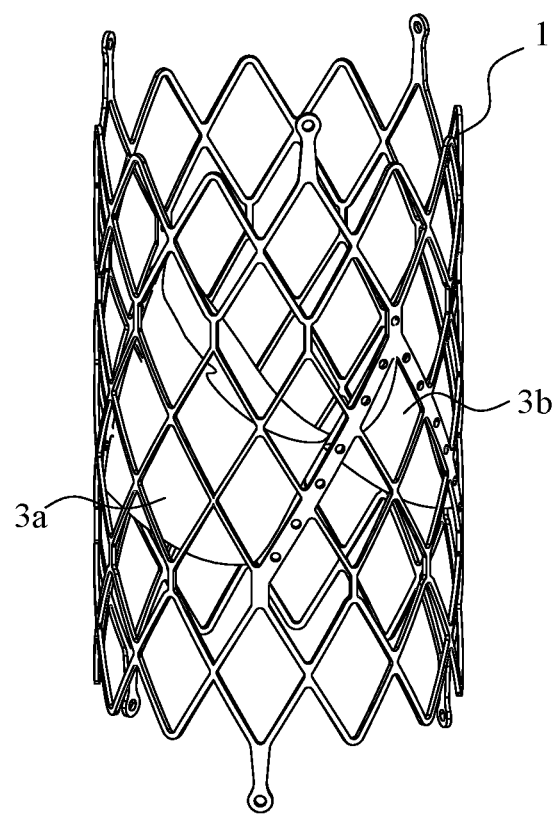
Figure 17D:
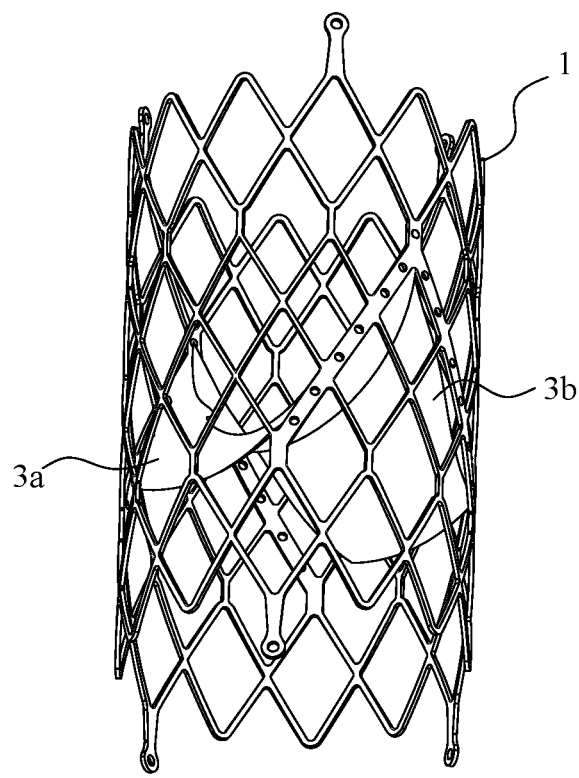

The two fixed rods may meet at the apex of the V-shaped configuration. In other embodiments, as shown in FIG. 16d, the two fixed rods may respectively extend to the neighbouring of the apex of the V-shaped configuration. In other words, the fixed rod 11 and the fixed rod 12 are not directly intersected. However, the overall shape of the fixed rod 11 and the fixed rod 12 may be regarded as V shape.

In practice, the apex of the V-shape configuration directs the downstream of the direction of normal blood flow. The two sides of the fixed edge of the same leaflet are stitched on different fixed strips, instead of two fixed rods of the same fixed strip.

The same fixed rod is provided with a plurality of threading holes distributed at intervals, such as 3 to 10 threading holes. For example, 6 threading holes are provided on the fixed rod 12 as shown in FIG. 16a. If the threading hole at the intersection of the fixed rods 11 is also regarded as one of the threading holes, the fixed rod 12 as shown in FIG. 16a is provided with 7 threading holes. In other embodiments, for example, the fixed rod 12 as shown in FIG. 16d is provided with 4 threading holes.

The stent 1 may have a grid structure, and the threading holes may be divided into multiple sets. The same set of threading holes is provided on the same fixed rod. The same set of threading holes 13 spans two to six grids relative to the grid structure of the support 1. The threading holes 13 are provided according to the predetermined stitching intervals and the extension direction of the fixed edge, which can greatly reduce the difficulty of stitching the fixed edge, improve the processing efficiency, and reduce the defective rate.

For example, in the embodiment shown in FIG. 16a, the threading holes on the fixed rod 12 spans three grids, namely grid Y1, grid Y2, and grid Y3 shown in FIG. 16a.

For example, in the embodiment shown in FIG. 16d, the threading hole on the fixed rod 12 spans two grids, namely grid Y1 and grid Y2 shown in FIG. 16d.

Referring to FIGS. 17a to 17d, since the fixed edge is generally parabolic, and the ends of the fixed edges of the two leaflets are substantially intersected with each other, in one embodiment, two V-shaped fixed strips may be provided on the stent, one of which including a fixed rod 11a and a fixed rod 12a that are intersected at the apex E1.

The other fixed strip includes a fixed rod 11b and a fixed rod 12b that are intersected at the apex E2. The two V-shaped fixing strips may be arranged at intervals or continuously distributed in the circumferential direction.

Two leaflets are provided. The fixed edge of each leaflet is stitched on the stent 1, and the movable edge is provided with two flaps 33 that are symmetrically distributed. When the two leaflets are closed, the movable edges and also the flaps respectively overlap with each other. It is also possible to combine with the aforementioned embodiments. For example, when the two leaflets are closed, the movable edges and the flaps may respectively partially overlap with each other.

The fixed edge of the leaflet 3a may be divided into two opposite sides with respect to the apex of the fixed edge, one side is stitched to the fixed rod 11a, and the other side is stitched to the fixed rod 11b.

Similarly, the fixed edge of the leaflet 3b may be divided into two opposite sides with respect to the apex of the fixed edge, one side is stitched to the fixed rod 12a, and the other side is stitched to the fixed rod 12b. In other words, the two fixed rods of the same fixing strip correspond to two different leaflets.

In the closed configuration, the movable edges of the leaflet 3a and the leaflet 3b attach to each other at the intersection line 3c of the movable edges. In the case where the two leaflets are symmetrically distributed, the intersection line 3c of the movable edges intersects with the axis of the stent. In the case where the two leaflets are asymmetrically distributed, especially in the case where the radial spans of the two leaflets are different, the intersection line 3c of the movable edges is offset from the axis of the stent.

In one embodiment, the stent 1 is formed by a plurality of intersected supporting bars. The stent 1 in this embodiment is formed by cutting a tube, and the plurality of supporting bars are intersected and form a grid structure.

Some of the supporting bars are locally widened, and the fixed rods are formed at the widened portions. For example, the fixed rod 11 and the fixed rod 12 are a part of the supporting bar itself. However, the width of the fixed rod 11 and the fixed rod 12 is increased relative to that of the portions of the supporting bars without threading holes, which is convenient to the provision of the threading holes.

The fixed strip may generally extend with a consistent width. In other words, the widths of several grids where threading holes are provided are the same. Alternatively, it is possible to only widen the portions where threading holes are provided. In other words, the widths vary at different portions. Preferably, the fixed rod extends with a consistent width for convenience of processing.

The fixing strip, as a part of the supporting bar (i.e., the part where the threading holes are provided), has a width ranging from 2 to 5 mm.

Figure 18A:
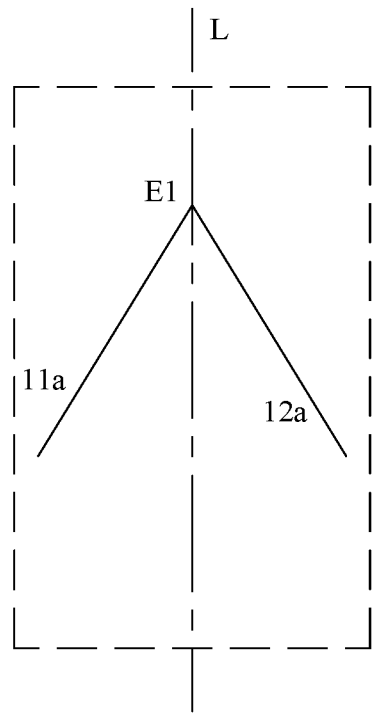
FIGS. 18a to 18c are respective schematic views of the fixing strips on the venous valve replacement device in one embodiment where the leaflets are symmetrical.
Figure 18B:
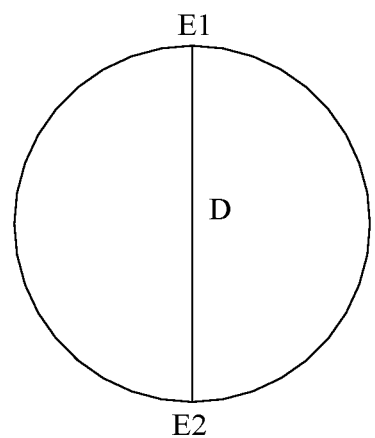
Figure 18C:
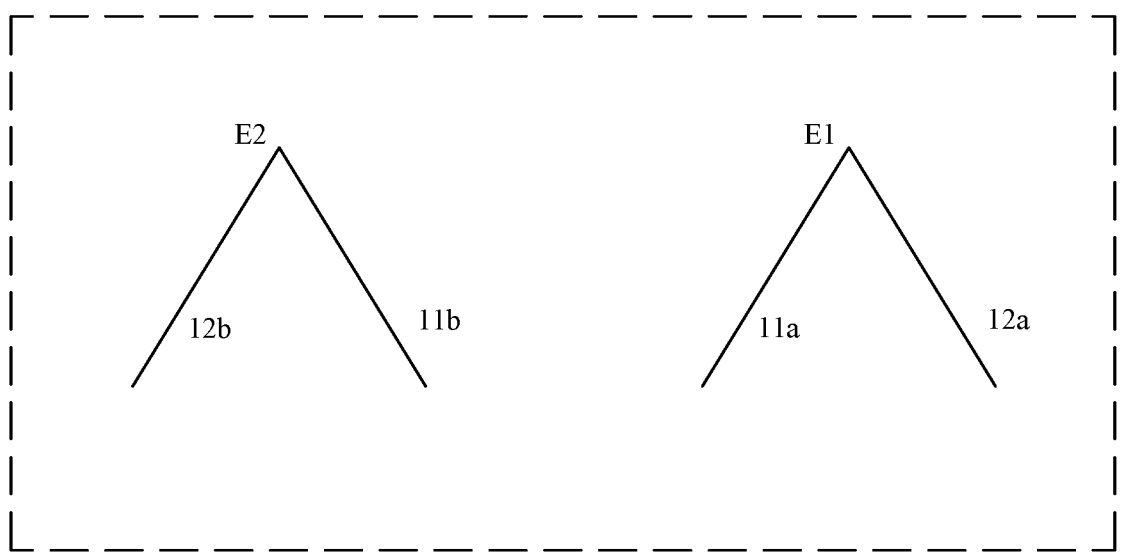

Referring to FIGS. 18a to 18c, the dashed box represents the outer profile of the stent viewed from the direction perpendicular to the paper of the drawing, and the same applies to other similar drawings. When the two leaflets are symmetrically distributed, two V-shaped fixed strips are symmetrically distributed on both sides of the axis of the stent, and the connection line between E1 and E2 is the diameter of the stent, and the length between E1 and E2 is equal to the length D of the diameter.

The fixed rod 11a and the fixed rod 12a intersecting at E1 are also symmetrically distributed on both sides of E1. After the stent is flattened, as shown in FIG. 18c, the two V-shaped fixed strips are distributed at an interval.

Figure 19A:
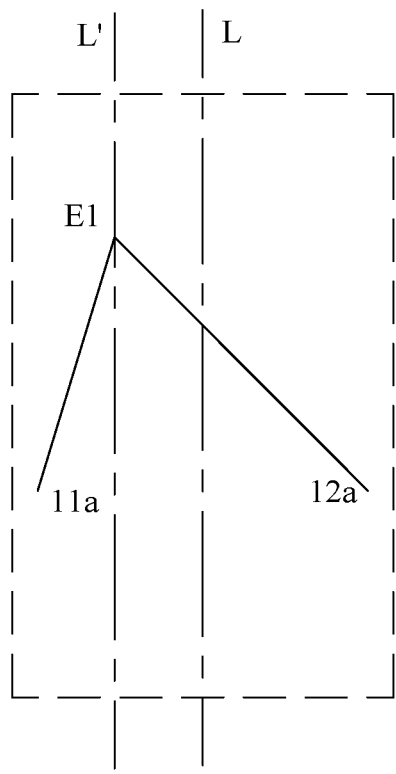
FIGS. 19a to 19c are respective schematic views of the fixing strips on the venous valve replacement device in one embodiment where the leaflets are asymmetric.
Figure 19B:
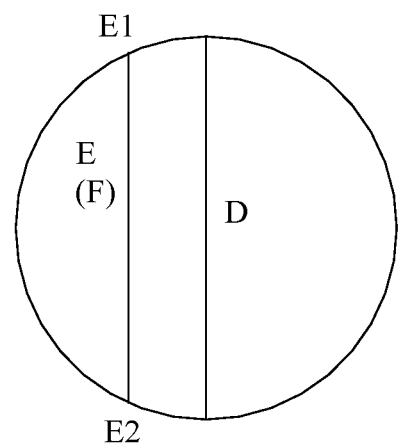
Figure 19C:
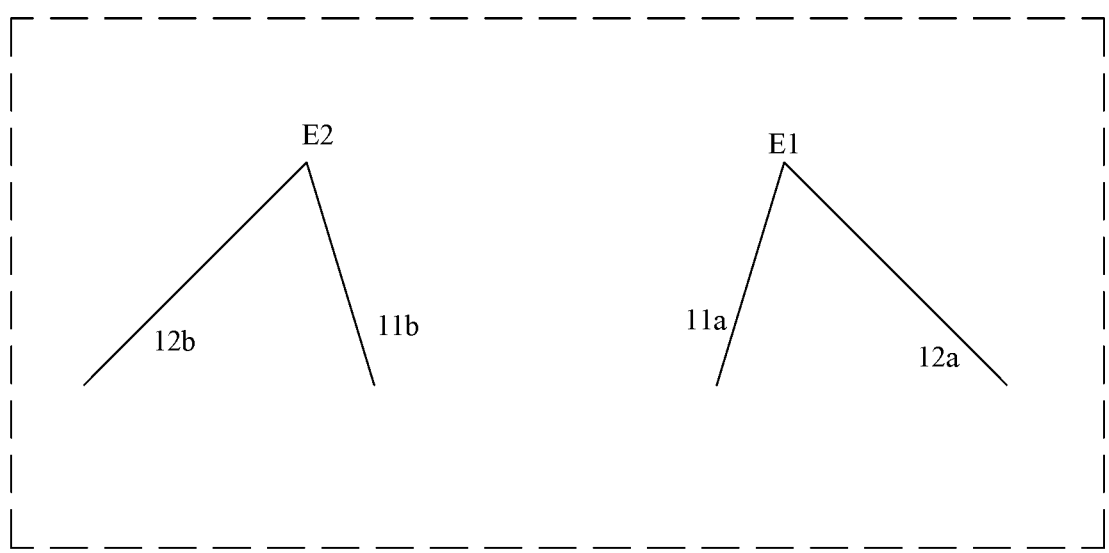

Referring to FIGS. 19a to 19c, in some embodiments, the two leaflets are asymmetrically distributed, and the distributions of the fixed strips and the fixed rods are also adjusted accordingly. For example, viewed along the axis of the stent, as shown in FIG. 19b, the connection line of the apexes of the two V-shaped fixed strips is designated as a reference line, which is offset from the axis of the stent.

The reference line is the line connecting E1 and E2, which can also be understood as the intersection line of the movable edges of the two leaflets in the closed configuration. The length E of the connection line between E1 and E2 is the same as the length F of the intersection line of the movable edges. Since the connection line between E1 and E2 is offset from the axis of the stent, the length E is less than the length D of the diameter.

As shown in FIG. 19a, viewed from the intersection line of the movable edges, the reference line, i.e., E1, is offset from the axis L, and the offset distance is the distance between the line L' and the axis L.

The ratio between the length of the reference line and the diameter of the stent reflects the offset degree to a certain extent. In one embodiment, the length E of the reference line and the length D of the diameter satisfy: $0.6\ D \leq E < 1\ D$;

In the case where the diameter of the stent changes at different axial positions, the ratio between the length of the reference line and the diameter of the stent may be referred to using the foregoing description of the relationship between the length of the intersecting line of the movable edges and the length of the diameter. For example, the axial position corresponding to the diameter is the same as the axial position of the apex of the V-shaped configuration.

In a preferred embodiment, $0.7\ D \leq E \leq 0.95\ D$.

In the case where the two leaflets are asymmetrical, especially in the case where the lengths of the fixed edges are different, the two fixed rods of the same fixed strip are not of equal length. For example, the fixed rod 11a may be shorter than the fixed rod 12a. Combined with the aforementioned related large and small leaflets, the two sides of the fixed edge of the small leaflet may be stitched to the fixed rod 11a and the fixed rod 11b, respectively, and the two sides of the fixed edge of the large leaflet may be stitched to the fixed rod 12a and the fixed rod 12b, respectively.

When the stent is flattened, each fixed rod generally extends along a straight line. The two fixed rods of the same fixed strip, such as the fixed rod 11a and the fixed rod 12a, have different angles with the axis of the stent. The shorter fixed rod 11a has a smaller angle with the axis L, and the longer fixed rod 12a has a larger angle with the axis L.

The angel between the two fixed rods of the same fixed strip, for example, the angle between the fixed rod 11a and the fixed rod 12a, is greater than 0 degree and less than or equal to 60 degrees, for example, between 45 and 60 degrees.

In the case where the axial positions of the apexes of the fixed edges of the two leaflets are the same, the axial spans of the fixed rod 11a and the fixed rod 12a are approximately the same.

Figure 20A:
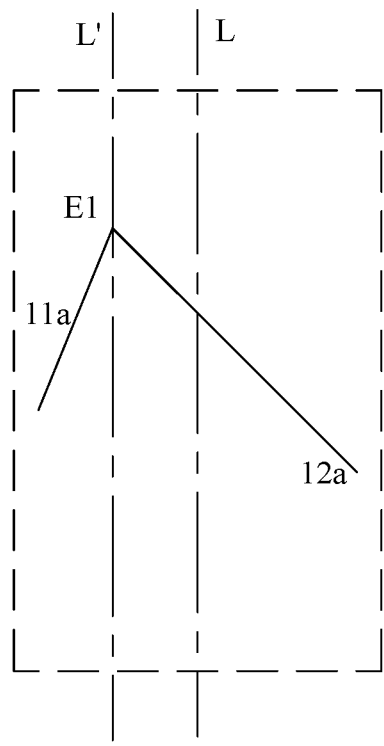
FIGS. 20a to 20c are respective schematic views of the fixing strips on the venous valve replacement device in another embodiment where the leaflets are asymmetrical.
Figure 20B:
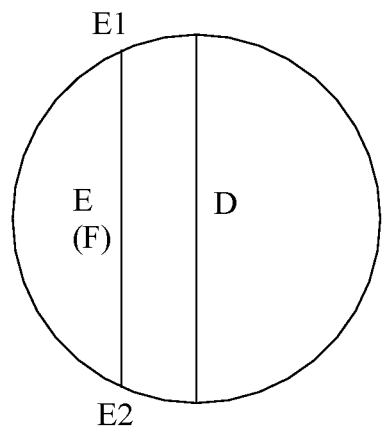
Figure 20C:
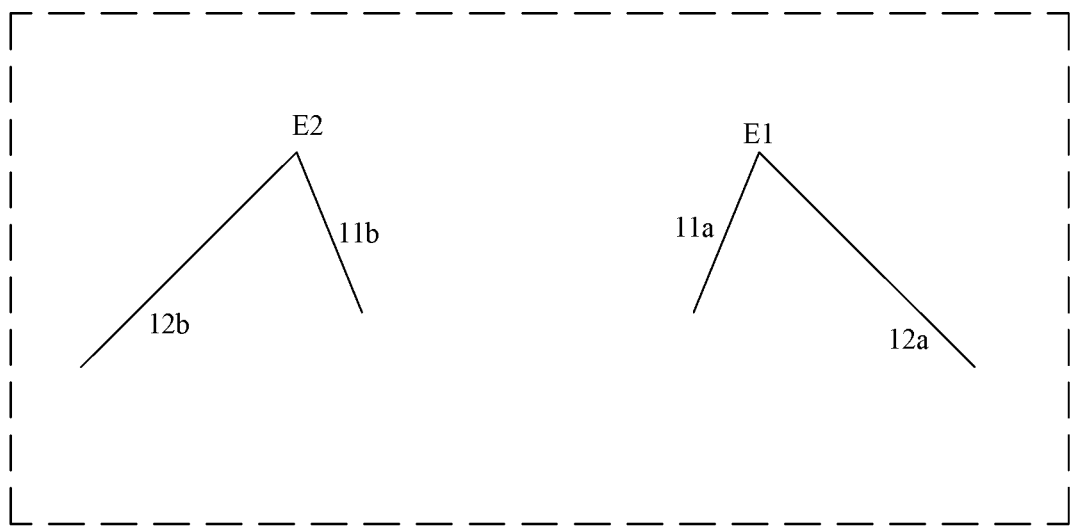

In some embodiments, the axial spans of the two leaflets are different. Referring to FIGS. 20a to 20c, the axial widths of the two fixed rods of the same fixed strip, for example, the axial widths of the fixed rod 11a and the fixed rod 12a, are different. Viewed from the FIGS. 20a to 20c, it can be understood as that the bottom end of the fixed rod 11a is higher than the bottom end of the fixed rod 12a.

In summary, depending on the profiles of the leaflets, the profiles of the fixing strips on the stent should also fit to that of the leaflets as much as possible, which reduces the difficulty of stitching, improves the processing efficiency, and further ensures the sealing performance.

The technical features of the above embodiments can be combined arbitrarily. In order to make the description concise, all possible combinations of the technical features in the above embodiments are not described. However, as long as the combination of these technical features does not have contradiction, this combination of these technical features should be regarded as falling within the scope of this specification.

When the technical features from different embodiments are shown in the same drawing, it can be regarded that the drawing also discloses the combination of the different embodiments.

The above disclosures are only specific implementations of the disclosure, but the disclosure is not limited thereto, and those skilled in the art can make various changes and modifications to the disclosure without departing from the spirit and scope of the disclosure. Obviously, these changes and modifications should fall within the protection scope required by this disclosure. In addition, although some specific terms are used in this specification, these terms are only for convenience of description and do not constitute any special restrictions on this disclosure.

What is claimed is:

1. A venous valve replacement device, comprising a stent with a blood flow channel and two leaflets connected to the stent, wherein one side of each leaflet is configured as a fixed edge connected with the stent, and the other side is configured as a movable edge, and wherein the movable edge and the fixed edge are connected by a patch, and the movable edge is provided with a notch adjacent to the patch to increase a relative degree of freedom; and wherein the movable edges of the two leaflets cooperates with each other to open or close the blood flow channel, and the movable edges of the two leaflets are provided with flaps that attach to each other in a closed configuration.

2. The venous valve replacement device according to claim 1, wherein the flap protrudes from the corresponding movable edge, and wherein a middle portion of the movable edge protrudes toward the fixed edge or protrudes away from the fixed edge, and an apex of the protruding portion is an apex of the movable edge.

3. The venous valve replacement device according to claim 2, wherein the same leaflet is provided with two flaps, and the two flaps are respectively located on both sides of the apex of the movable edge.

4. The venous valve replacement device according to claim 1, wherein the fixed edge is shaped as a parabola, wherein an apex of the parabola is located at an upstream of a normal blood flow, and the fixed edge gradually extends towards a downstream of the normal blood flow from the apex of the parabola on both sides.

5. The venous valve replacement device according to claim 1, wherein in the closed configuration, the movable edge extends in a two-dimensional plane, and wherein in the closed configuration, a projection of the movable edge along an axial direction of the stent is a straight line segment.

6. The venous valve replacement device according to claim 1, wherein in a flattened configuration of the leaflet, a middle portion of the fixed edge protrudes away from the movable edge, and an apex of a protruding portion at the middle portion of the fixed edge is an apex of the fixed edge, and an apex of a protruding portion at a middle portion of the movable edge is an apex of the movable edge.

7. The venous valve replacement device according to claim 6, wherein a line connecting the apex of the movable edge and the apex of the fixed edge is a centerline of the leaflet, and wherein portions of the movable edge and the fixed edge on the same side of the centerline of the leaflet are gradually closer to each other and are connected by the patch, which is connected to the stent.

8. The venous valve replacement device according to claim 1, wherein the movable edge comprises a mouth section located near an apex of the movable edge, and guide sections respectively located on both sides of the mouth section, wherein a radial outward extending rate of the mouth section is V1, a radial outward extending rate of the guide section is V2, and V1 is greater than V2; and wherein
the radial outward extending rate is a variation of a radial position when extending for a unit distance along an axial direction of the stent; and wherein
in the closed configuration, the mouth sections of the two leaflets overlap with each other fully or partially; and wherein
in an opened configuration, the mouth sections of the movable edges of the two leaflets are completely separated from each other.

9. The venous valve replacement device according to claim 8, wherein in the closed configuration, a span of the mouth section in a radial direction of the stent is at least ⅔ times of a diameter of the stent at the leaflets.

10. The venous valve replacement device according to claim 8, wherein the flap is located at a junction of the mouth section and the guide section.

11. The venous valve replacement device according to claim 8, wherein the leaflet comprises a middle portion corresponding to the mouth section and side portions corresponding to the guide sections, wherein in the closed configuration, the side portion extends towards and get closer to an inner wall of the stent.

12. The venous valve replacement device according to claim 1, wherein an inner wall of the stent is further provided with a covering film, and wherein the covering film is located at an upstream of the leaflets, and an end of the covering film facing the leaflets is connected to the fixed edges of the leaflets to form the blood flow channel.

13. The venous valve replacement device according to claim 12, wherein a plurality of cutting areas are provided at intervals at an edge of an end of the covering film away from the leaflets.

14. The venous valve replacement device according to claim 1, wherein the two leaflets have different radial spans, wherein the leaflet with a larger radial span is a large leaflet, and the leaflet with a smaller radial span is a small leaflet, and an intersection line of the movable edges of the two leaflets in the closed configuration is offset from an axis of the stent; and
in the closed configuration, a projection of the intersection line of the movable edges of the two leaflets along an axial direction of the stent is shaped as a straight line segment, and an extension direction of the radial span is perpendicular to the straight line segment.

15. The venous valve replacement device according to claim 1, wherein the two leaflets have different axial spans along an axis of the stent, and wherein in a flattened configuration of the leaflet, a middle portion of the fixed edge protrudes away from the movable edge, and an apex of a protruding portion at the middle portion of the fixed edge is an apex of the fixed edge, and projections of the apexes of the fixed edges of the leaflets on the axis of the stent are offset from each other.

16. The venous valve replacement device according to claim 15, wherein the two leaflets have different radial spans, wherein the leaflet with a larger radial span is a large leaflet, and the leaflet with a smaller radial span is a small leaflet, and an intersection line of the movable edges of the two leaflets in the closed configuration is offset from the axis of the stent; and in the closed configuration, a projection of the intersection line of the movable edges of the two leaflets along an axial direction of the stent is shaped as a straight line segment, and an extension direction of the radial span is perpendicular to the straight line segment; and along a direction of a normal blood flow in practice, the apex of the fixed edge of the large leaflet is located at an upstream, and the apex of the fixed edge of the small leaflet is located at a downstream.

17. The venous valve replacement device according to claim 1, wherein the stent is provided with threading holes for connecting the fixed edges of the leaflets, and wherein the stent is provided with two V-shaped fixing strips, and the threading holes are distributed at corresponding positions of the fixing strips; and an apex of the V-shape fixing strip directs to a downstream of a direction of a normal blood flow in practice, and two sides of the fixed edge of the same leaflet are stitched on different fixing strips.

18. The venous valve replacement device according to claim 17, wherein the V-shaped fixing strip comprises two fixed rods; wherein in a flattened configuration of the stent, the two fixed rods are oblique to each other, and the two fixed rods of the same fixing strip respectively correspond to different leaflets, wherein the two fixed rods intersect at the apex of the V-shaped fixing strip or respectively extend to a neighboring of the apex of the V-shaped fixing strip.

19. The venous valve replacement device according to claim 17, wherein the two V-shaped fixing strips are arranged at intervals in a circumferential direction of the stent.

* * * * *